(12) United States Patent  
Chelak et al.

(10) Patent No.: US 8,496,627 B2
(45) Date of Patent: Jul. 30, 2013

(54) PASSIVE LATCH RING SAFETY SHIELD FOR INJECTION DEVICES

(75) Inventors: Todd M. Chelak, Westborough, MA (US); Alan Bachman, Milford, CT (US)

(73) Assignee: Covidien LP, Mansfield, MA (US)

( * ) Notice: Subject to any disclaimer, the term of this patent is extended or adjusted under 35 U.S.C. 154(b) by 1530 days.

(21) Appl. No.: 11/726,169

(22) Filed: Mar. 21, 2007

(65) Prior Publication Data

US 2007/0239117 A1 Oct. 11, 2007

Related U.S. Application Data

(60) Provisional application No. 60/784,558, filed on Mar. 21, 2006, provisional application No. 60/848,205, filed on Sep. 29, 2006.

(51) Int. Cl.
*A61M 5/32* (2006.01)

(52) U.S. Cl.
USPC .......................................................... 604/198

(58) Field of Classification Search
USPC .................................. 604/110, 192, 197, 198
See application file for complete search history.

(56) References Cited

U.S. PATENT DOCUMENTS

| | | |
|---|---|---|
| 1,779,451 A | 10/1930 | Sponsel |
| 2,559,474 A | 7/1951 | Son |
| 2,700,385 A | 1/1955 | Ortiz |
| 2,836,942 A | 6/1958 | Miskel |
| 2,854,976 A | 10/1958 | Heydrich |
| 2,953,243 A | 9/1960 | Roehr |
| 3,021,942 A | 2/1962 | Hamilton |
| 3,073,307 A | 1/1963 | Stevens |
| 3,074,542 A | 1/1963 | Myerson et al. |
| 3,255,873 A | 6/1966 | Speelman |
| 3,294,231 A | 12/1966 | Vanderbeck |
| 3,323,523 A | 6/1967 | Scislowicz et al. |
| 3,329,146 A | 7/1967 | Waldman, Jr. |
| 3,333,682 A | 8/1967 | Burke |
| 3,367,488 A | 2/1968 | Hamilton |
| 3,485,239 A | 12/1969 | Vanderbeck |
| 3,537,452 A | 11/1970 | Wilks |
| 3,587,575 A | 6/1971 | Lichtenstein |

(Continued)

FOREIGN PATENT DOCUMENTS

| | | |
|---|---|---|
| EP | 0 144 483 A2 | 6/1985 |
| EP | 0 344 606 A2 | 12/1989 |

(Continued)

*Primary Examiner* — Kevin C Sirmons
*Assistant Examiner* — Bradley Osinski
(74) *Attorney, Agent, or Firm* — Lisa E. Winsor, Esq.

(57) ABSTRACT

A passive latch ring safety shield for use with medical injection devices is disclosed. The safety shield includes an inner sheath defining a channel which is dimensioned to receive an injection device and an outer sheath defining a channel which is dimensioned to slidably receive the inner sheath. A biasing member is provided between the inner and outer sheaths to urge the outer sheath in relation to the inner sheath from a retracted position to an advanced position. A resilient latch ring is supported on the safety shield in a position to prevent movement of the outer sheath in relation to the inner sheath from a retracted to and advanced position. The latch ring is deformable in response to actuation of the injection device to disengage the outer sheath from the inner sheath and allow the biasing member to move the outer sheath from the retracted position to the advanced position in relation to the inner sheath.

34 Claims, 35 Drawing Sheets

U.S. PATENT DOCUMENTS

| | | |
|---|---|---|
| 3,610,240 A | 10/1971 | Harautuneian |
| 3,645,835 A | 2/1972 | Hodgson |
| 3,658,061 A | 4/1972 | Hall |
| 3,828,775 A | 8/1974 | Armel |
| 3,840,008 A | 10/1974 | Noiles |
| 3,890,971 A | 6/1975 | Leeson et al. |
| 3,904,033 A | 9/1975 | Haerr |
| 3,918,446 A | 11/1975 | Buttaravoli |
| 3,934,722 A | 1/1976 | Goldberg |
| 3,968,876 A | 7/1976 | Brookfield |
| 4,040,419 A | 8/1977 | Goldman |
| 4,106,621 A | 8/1978 | Sorenson |
| 4,113,090 A | 9/1978 | Carstens |
| 4,139,009 A | 2/1979 | Alvarez |
| 4,175,008 A | 11/1979 | White |
| 4,270,536 A | 6/1981 | Lemelson |
| 4,300,678 A | 11/1981 | Gyure et al. |
| 4,375,849 A | 3/1983 | Hanifl |
| 4,430,082 A | 2/1984 | Schwabacher |
| 4,592,744 A | 6/1986 | Jagger et al. |
| 4,634,428 A | 1/1987 | Cuu |
| 4,643,722 A | 2/1987 | Smith, Jr. |
| 4,659,330 A | 4/1987 | Nelson et al. |
| 4,664,259 A | 5/1987 | Landis |
| 4,664,654 A | 5/1987 | Strauss |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Cholesi |
| 4,738,663 A | 4/1988 | Bogan |
| 4,743,233 A | 5/1988 | Schneider |
| 4,747,836 A | 5/1988 | Luther |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,790,828 A | 12/1988 | Dombrowski et al. |
| 4,795,432 A | 1/1989 | Karczmer |
| 4,795,443 A | 1/1989 | Permenter et al. |
| 4,801,295 A | 1/1989 | Spencer |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byrne et al. |
| 4,826,491 A | 5/1989 | Schramm |
| 4,838,871 A | 6/1989 | Luther |
| 4,840,619 A | 6/1989 | Hughes |
| 4,842,587 A | 6/1989 | Poncy |
| 4,846,796 A | 7/1989 | Carrell et al. |
| 4,846,811 A | 7/1989 | Vanderhoof |
| 4,850,968 A | 7/1989 | Romano |
| 4,850,976 A | 7/1989 | Heinrich et al. |
| 4,850,977 A | 7/1989 | Bayless |
| 4,850,978 A | 7/1989 | Dudar et al. |
| 4,850,994 A | 7/1989 | Zerbst et al. |
| 4,850,996 A | 7/1989 | Cree |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,867,172 A | 9/1989 | Haber et al. |
| 4,867,746 A | 9/1989 | Dufresne |
| 4,872,552 A | 10/1989 | Unger |
| 4,874,382 A | 10/1989 | Lindemann et al. |
| 4,874,383 A | 10/1989 | McNaughton |
| 4,874,384 A * | 10/1989 | Nunez ............ 604/198 |
| 4,883,469 A | 11/1989 | Glazier |
| 4,886,503 A | 12/1989 | Miller |
| 4,887,998 A | 12/1989 | Martin et al. |
| 4,888,001 A | 12/1989 | Schoenberg |
| 4,892,107 A | 1/1990 | Haber |
| 4,892,521 A | 1/1990 | Laico et al. |
| 4,898,589 A | 2/1990 | Dolgin et al. |
| 4,900,309 A | 2/1990 | Netherton et al. |
| 4,904,244 A | 2/1990 | Harsh et al. |
| 4,911,694 A | 3/1990 | Dolan |
| 4,911,706 A | 3/1990 | Levitt |
| 4,927,018 A | 5/1990 | Yang et al. |
| 4,929,241 A | 5/1990 | Kulli |
| 4,935,012 A | 6/1990 | Magre et al. |
| 4,935,013 A | 6/1990 | Haber et al. |
| 4,936,830 A | 6/1990 | Verlier |
| 4,944,397 A | 7/1990 | Miller |
| 4,944,731 A | 7/1990 | Cole |
| 4,950,249 A | 8/1990 | Jagger et al. |
| 4,950,250 A | 8/1990 | Haber et al. |
| 4,966,589 A | 10/1990 | Kaufman |
| 4,978,344 A | 12/1990 | Dombrowski et al. |
| 4,982,842 A | 1/1991 | Hoilister |
| 4,985,021 A | 1/1991 | Straw et al. |
| 4,994,041 A | 2/1991 | Dombrowski et al. |
| 5,000,744 A | 3/1991 | Hoffman et al. |
| 5,015,240 A | 5/1991 | Soproni et al. |
| 5,057,089 A | 10/1991 | Greco |
| 5,059,180 A | 10/1991 | McLees |
| 5,092,851 A | 3/1992 | Ragner |
| 5,108,379 A | 4/1992 | Dolgin et al. |
| RE34,045 E | 8/1992 | McFarland |
| 5,135,509 A | 8/1992 | Olliffe |
| 5,139,489 A | 8/1992 | Hollister |
| 5,147,303 A | 9/1992 | Martin |
| 5,154,285 A | 10/1992 | Hollister |
| 5,176,655 A | 1/1993 | McCormick et al. |
| 5,176,656 A | 1/1993 | Bayless |
| 5,193,552 A | 3/1993 | Columbus et al. |
| 5,195,983 A | 3/1993 | Boese |
| 5,209,739 A | 5/1993 | Talalay |
| 5,232,454 A | 8/1993 | Hollister |
| 5,232,455 A | 8/1993 | Hollister |
| 5,242,417 A | 9/1993 | Paudler |
| 5,242,418 A | 9/1993 | Weinstein |
| 5,246,427 A | 9/1993 | Sturman et al. |
| 5,246,428 A | 9/1993 | Falknor |
| 5,250,031 A | 10/1993 | Kaplan et al. |
| 5,254,099 A | 10/1993 | Kuractna et al. |
| 5,256,152 A | 10/1993 | Marks |
| 5,256,153 A | 10/1993 | Hake |
| 5,277,311 A | 1/1994 | Hollister |
| 5,290,255 A | 3/1994 | Vallelunga et al. |
| 5,304,137 A | 4/1994 | Fluke |
| 5,312,369 A | 5/1994 | Arcusin et al. |
| 5,334,158 A | 8/1994 | McLees |
| 5,348,544 A | 9/1994 | Sweeney et al. |
| 5,356,392 A | 10/1994 | Firth et al. |
| 5,372,589 A | 12/1994 | Davis |
| 5,403,283 A | 4/1995 | Luther |
| 5,403,286 A | 4/1995 | Lockwood, Jr. |
| 5,407,436 A | 4/1995 | Toft et al. |
| 5,411,492 A | 5/1995 | Sturman et al. |
| 5,423,765 A | 6/1995 | Hollister |
| 5,423,766 A | 6/1995 | Di Cesare |
| 5,425,720 A | 6/1995 | Rogalsky et al. |
| 5,445,618 A | 8/1995 | Adobbati |
| 5,447,501 A | 9/1995 | Karlsson et al. |
| 5,466,223 A | 11/1995 | Bressler et al. |
| 5,480,385 A | 1/1996 | Thome et al. |
| 5,487,733 A | 1/1996 | Caizza et al. |
| 5,487,734 A | 1/1996 | Thome et al. |
| 5,490,841 A | 2/1996 | Landis |
| 5,498,243 A | 3/1996 | Vallelunga et al. |
| 5,531,694 A | 7/1996 | Clemens et al. |
| 5,533,980 A | 7/1996 | Sweeney et al. |
| 5,536,240 A | 7/1996 | Edwards et al. |
| 5,538,508 A | 7/1996 | Steyn |
| 5,542,927 A | 8/1996 | Thorne et al. |
| 5,549,568 A | 8/1996 | Shields |
| 5,549,570 A | 8/1996 | Rogalsky |

| | | |
|---|---|---|
| 5,549,708 A | 8/1996 | Thome et al. |
| 5,562,629 A | 10/1996 | Haughton et al. |
| 5,562,631 A | 10/1996 | Bogert |
| 5,573,510 A | 11/1996 | Isaacson |
| 5,584,816 A | 12/1996 | Gyure et al. |
| 5,584,818 A | 12/1996 | Morrison |
| 5,599,318 A | 2/1997 | Sweeney et al. |
| 5,611,782 A | 3/1997 | Haedt |
| 5,643,220 A | 7/1997 | Cosme |
| 5,672,161 A | 9/1997 | Allen et al. |
| 5,681,291 A * | 10/1997 | Galli .................. 604/192 |
| 5,695,474 A | 12/1997 | Daugherty |
| 5,695,477 A | 12/1997 | Sfikas |
| 5,700,249 A | 12/1997 | Jenkins |
| 5,735,827 A | 4/1998 | Adwers et al. |
| 5,738,665 A | 4/1998 | Caizza et al. |
| 5,746,718 A | 5/1998 | Steyn |
| 5,746,726 A | 5/1998 | Sweeney et al. |
| 5,755,699 A | 5/1998 | Blecher et al. |
| 5,814,018 A | 9/1998 | Elson et al. |
| 5,817,064 A | 10/1998 | DeMarco et al. |
| 5,823,997 A | 10/1998 | Thome |
| 5,843,041 A | 12/1998 | Hake et al. |
| 5,879,330 A | 3/1999 | Bell |
| 5,885,249 A | 3/1999 | Irisawa |
| 5,910,130 A | 6/1999 | Caizza et al. |
| 5,919,168 A | 7/1999 | Wheeler |
| 5,921,969 A | 7/1999 | Vallelunga et al. |
| 5,925,020 A | 7/1999 | Nestell |
| 5,951,522 A | 9/1999 | Rosato et al. |
| 5,957,892 A | 9/1999 | Thome |
| 5,980,488 A | 11/1999 | Thome |
| 5,997,504 A | 12/1999 | Bell |
| 6,004,296 A * | 12/1999 | Jansen et al. .................. 604/198 |
| 6,015,397 A | 1/2000 | Elson et al. |
| 6,036,675 A | 3/2000 | Thome et al. |
| 6,149,629 A | 11/2000 | Wilson et al. |
| 6,171,284 B1 | 1/2001 | Kao et al. |
| RE37,110 E | 3/2001 | Hollister |
| 6,224,576 B1 | 5/2001 | Thorne et al. |
| RE37,252 E | 7/2001 | Hollister |
| 6,254,575 B1 | 7/2001 | Thome, Jr. et al. |
| 6,280,420 B1 | 8/2001 | Ferguson et al. |
| 6,334,857 B1 | 1/2002 | Hollister et al. |
| 6,582,397 B2 | 6/2003 | Alesi et al. |
| 6,635,032 B2 | 10/2003 | Ward, Jr. |
| 2001/0039401 A1 | 11/2001 | Ferguson et al. |
| 2002/0072716 A1 | 6/2002 | Barrus et al. |
| 2003/0004465 A1 | 1/2003 | Ferguson et al. |
| 2003/0212380 A1 | 11/2003 | Barrelle |
| 2005/0080383 A1 | 4/2005 | Woehr |

FOREIGN PATENT DOCUMENTS

| | | |
|---|---|---|
| EP | 0 457 477 B1 | 11/1991 |
| EP | 0 485 345 B1 | 5/1992 |
| EP | 0 585 391 B1 | 11/1992 |
| EP | 0 533 308 A1 | 3/1993 |
| EP | 0 626 924 B1 | 1/1994 |
| EP | 0 654 281 BI | 9/1994 |
| EP | 0 597 857 BI | 7/1995 |
| EP | 0 705 613 B1 | 4/1996 |
| EP | 0713710 A1 | 5/1996 |
| EP | 0 815 890 A2 | 9/1997 |
| EP | 0 815 888 A2 | 10/1997 |
| EP | 0 807 443 A2 | 11/1997 |
| EP | 0 832 659 A2 | 12/1997 |
| EP | 0 819 441 A1 | 1/1998 |
| EP | 0 603 365 B1 | 2/1998 |
| EP | 0 832 660 A2 | 4/1998 |
| EP | 1 092 443 A2 | 4/2001 |
| EP | 1 116 493 A1 | 7/2001 |
| GB | 1 233 302 | 5/1971 |
| GB | 2 283 429 A | 5/1995 |
| GB | 2 369 779 A | 6/2002 |
| JP | 10-076007 | 3/1998 |
| JP | 10-127765 | 5/1998 |
| WO | WO 87/07162 | 12/1987 |
| WO | WO 89/07955 | 9/1989 |
| WO | WO 93/17732 | 9/1993 |
| WO | WO 94/19036 | 9/1994 |
| WO | WO 97/31666 | 9/1997 |
| WO | WO 98/07463 | 2/1998 |
| WO | WO 98/10816 | 3/1998 |
| WO | WO 98/11928 | 3/1998 |
| WO | WO 98/13081 | 4/1998 |
| WO | WO 99/59660 | 11/1999 |
| WO | WO 00/16832 | 3/2000 |
| WO | WO 00/38765 | 7/2000 |
| WO | WO 01/32241 A1 | 5/2001 |
| WO | WO 01/32244 A1 | 5/2001 |
| WO | WO 01/36030 A1 | 5/2001 |

* cited by examiner

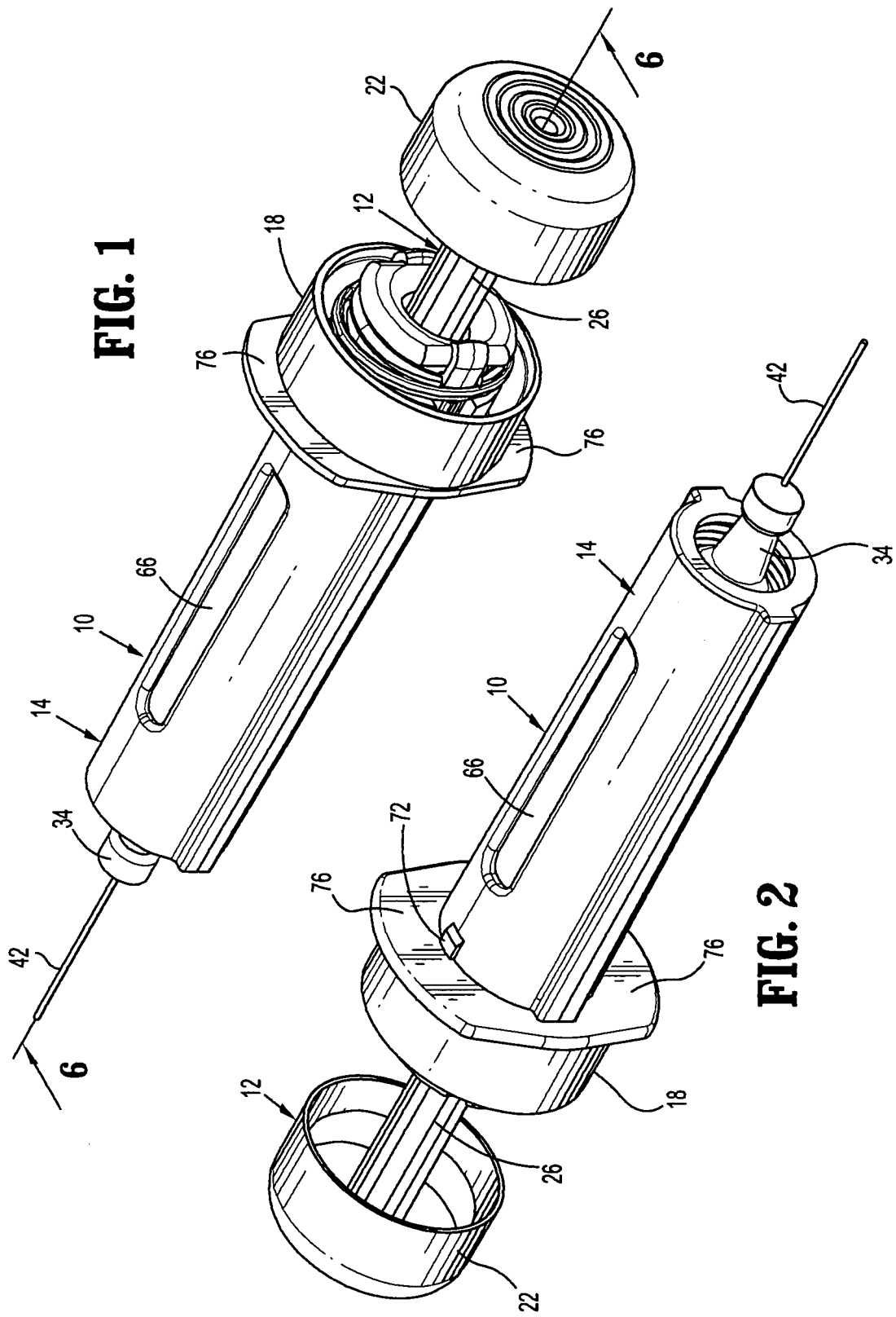

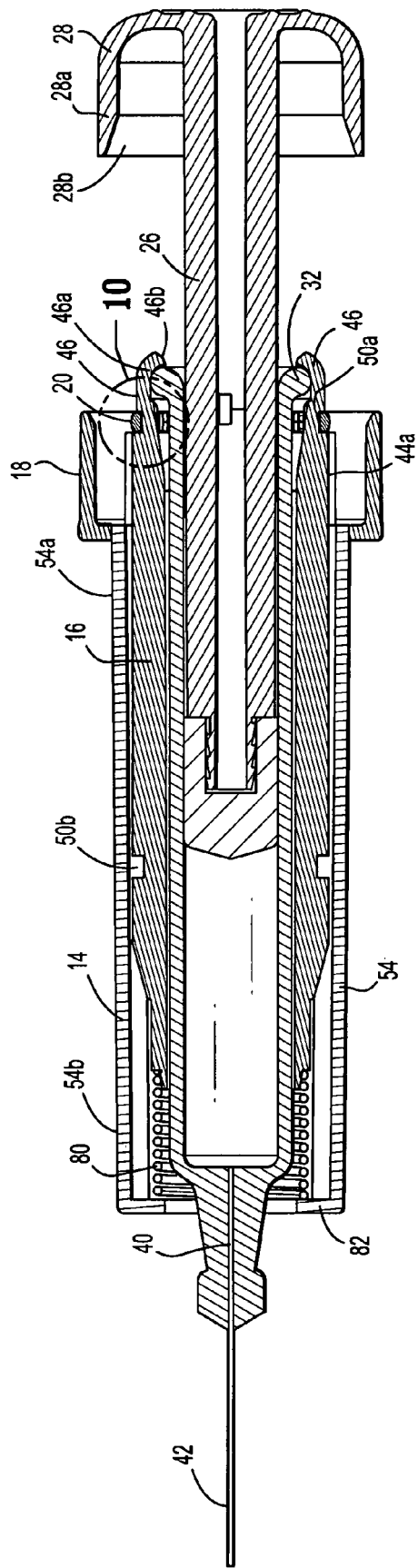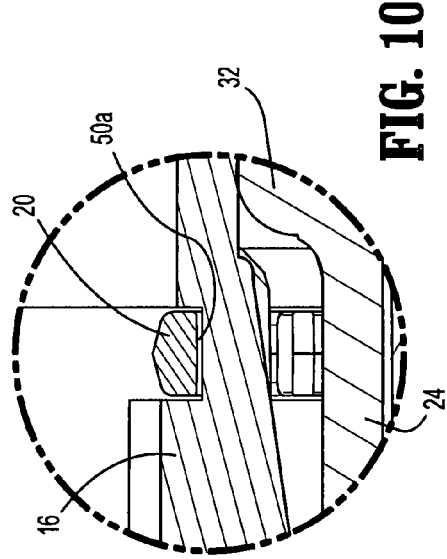
FIG. 9
FIG. 10

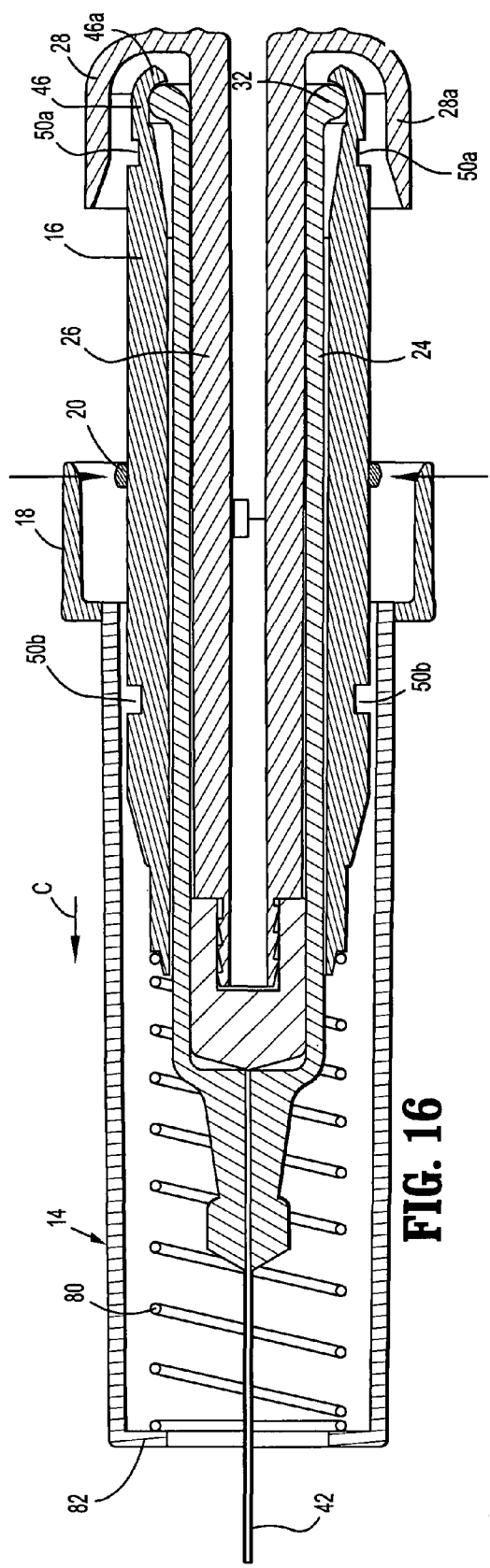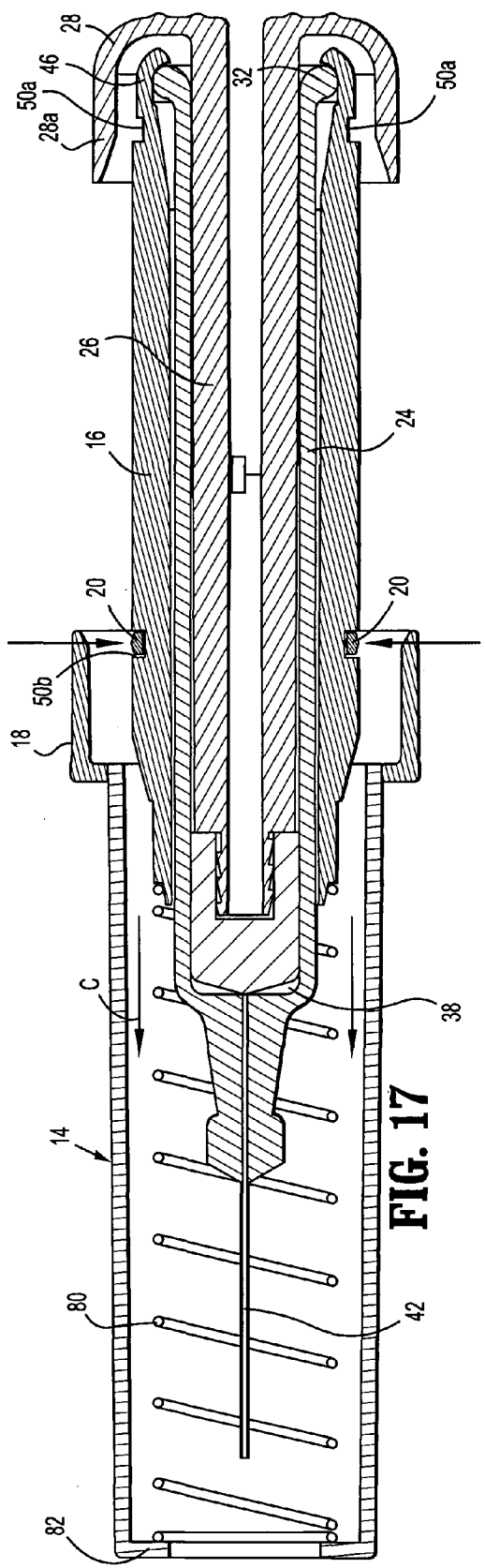

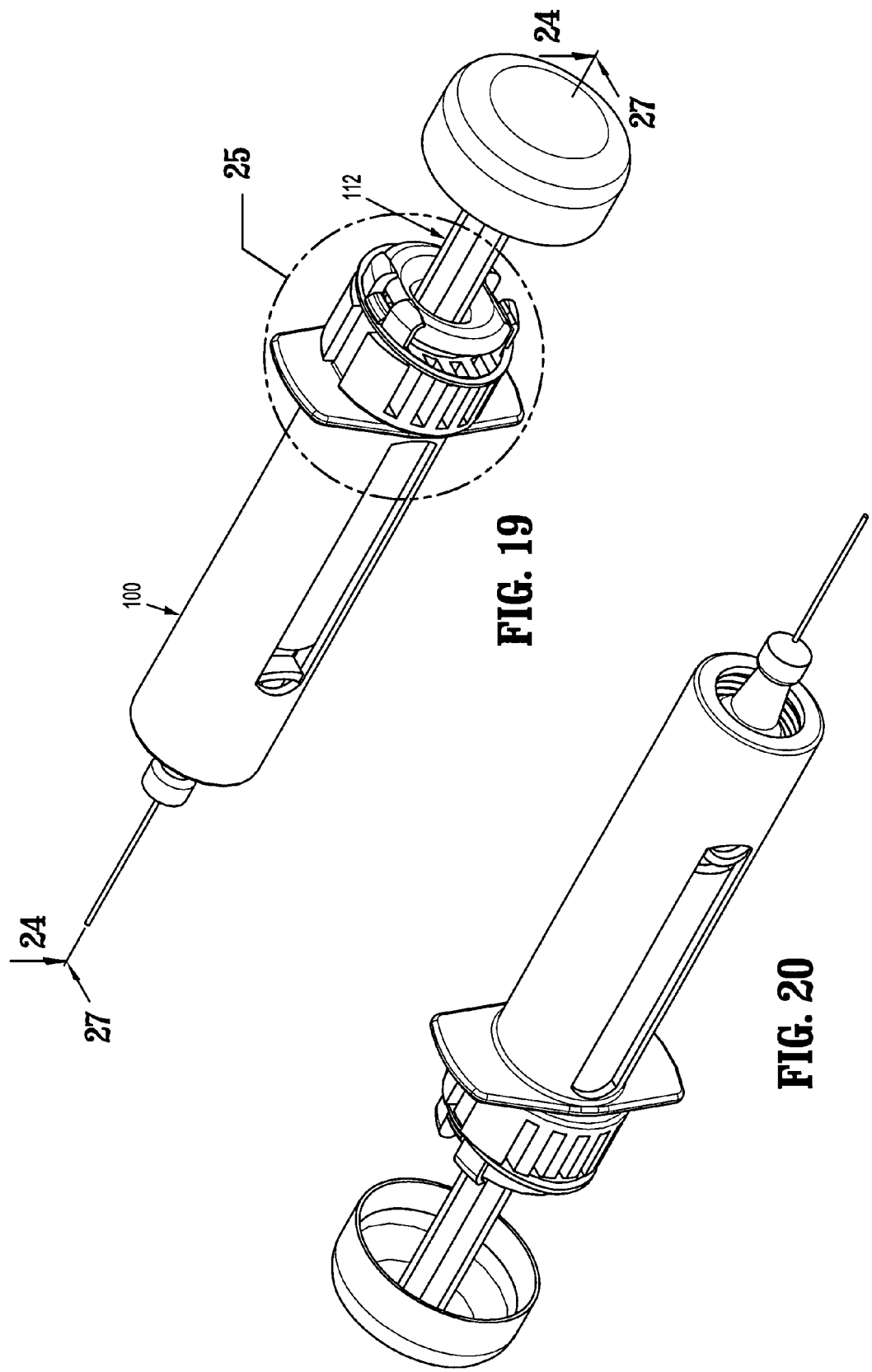

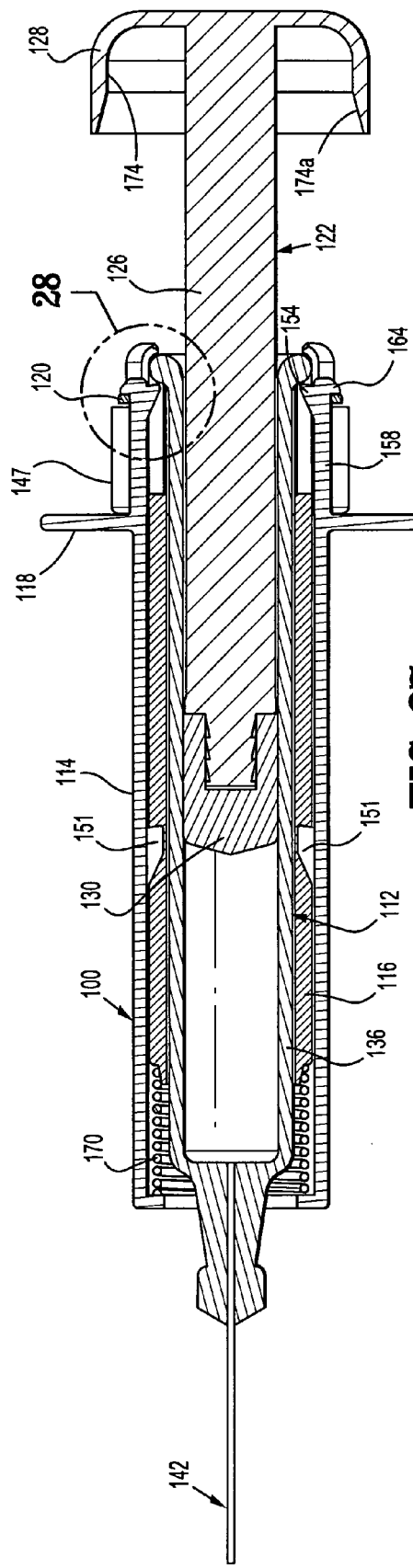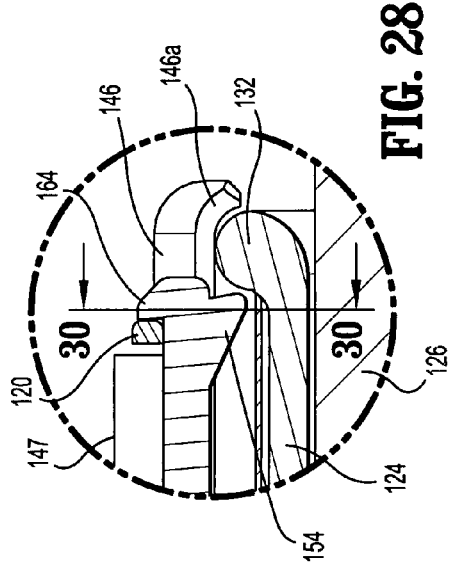

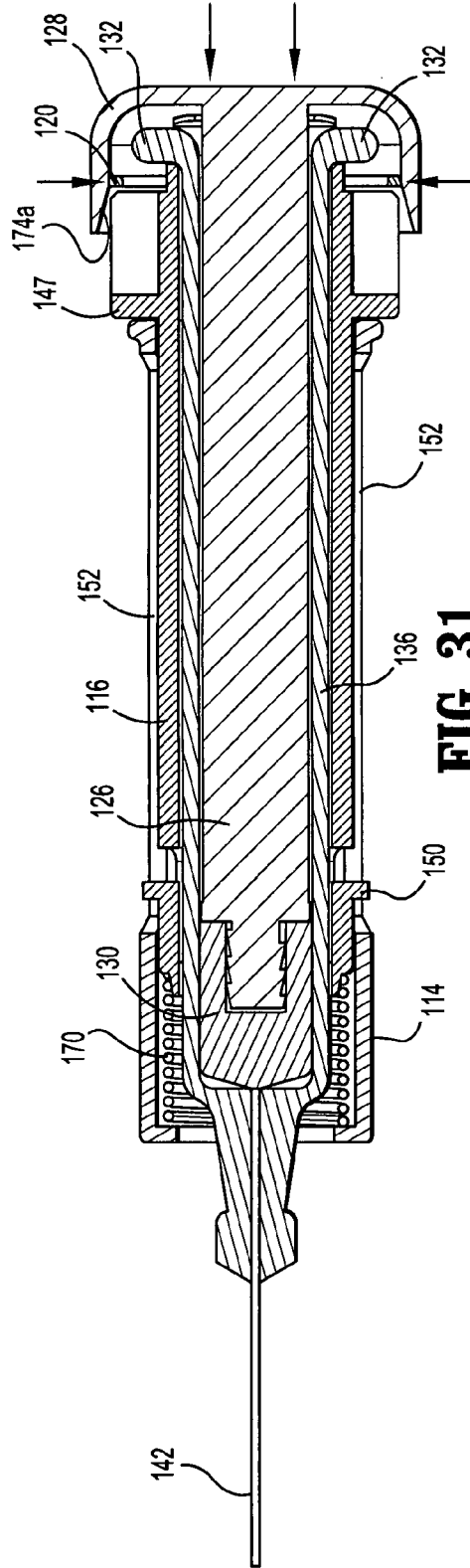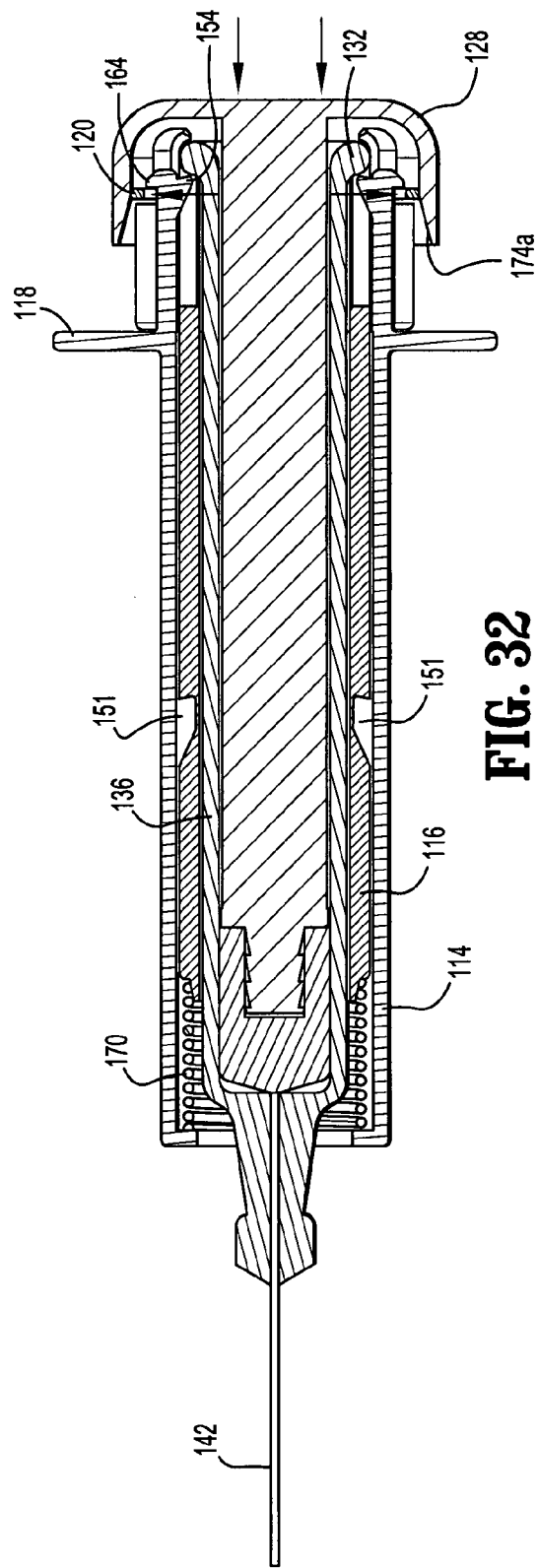
FIG. 31
FIG. 32

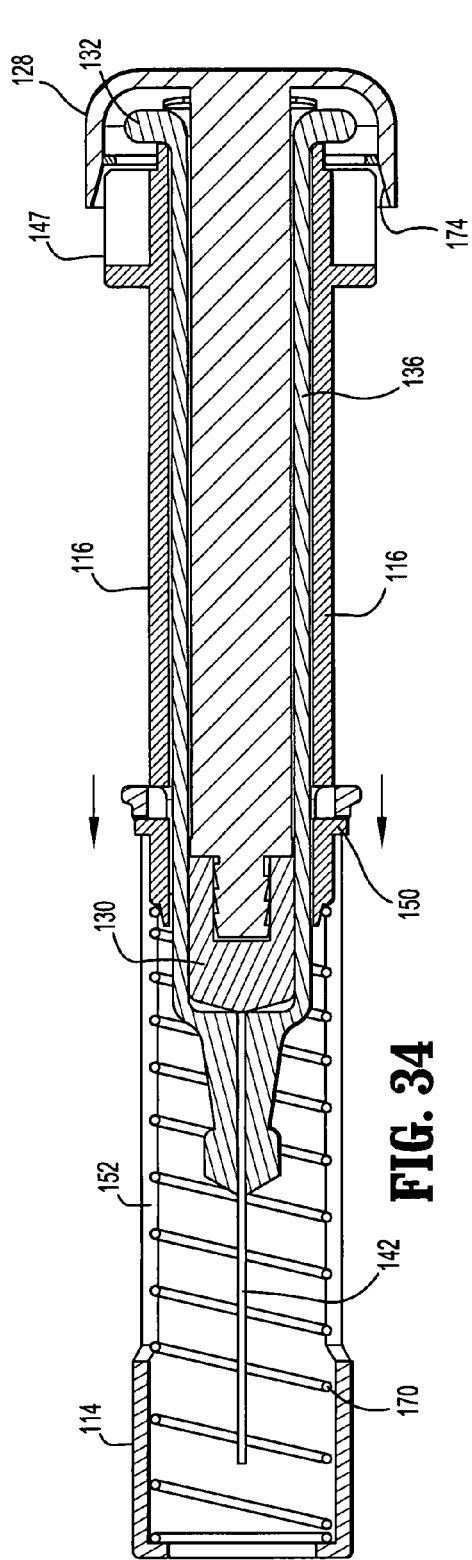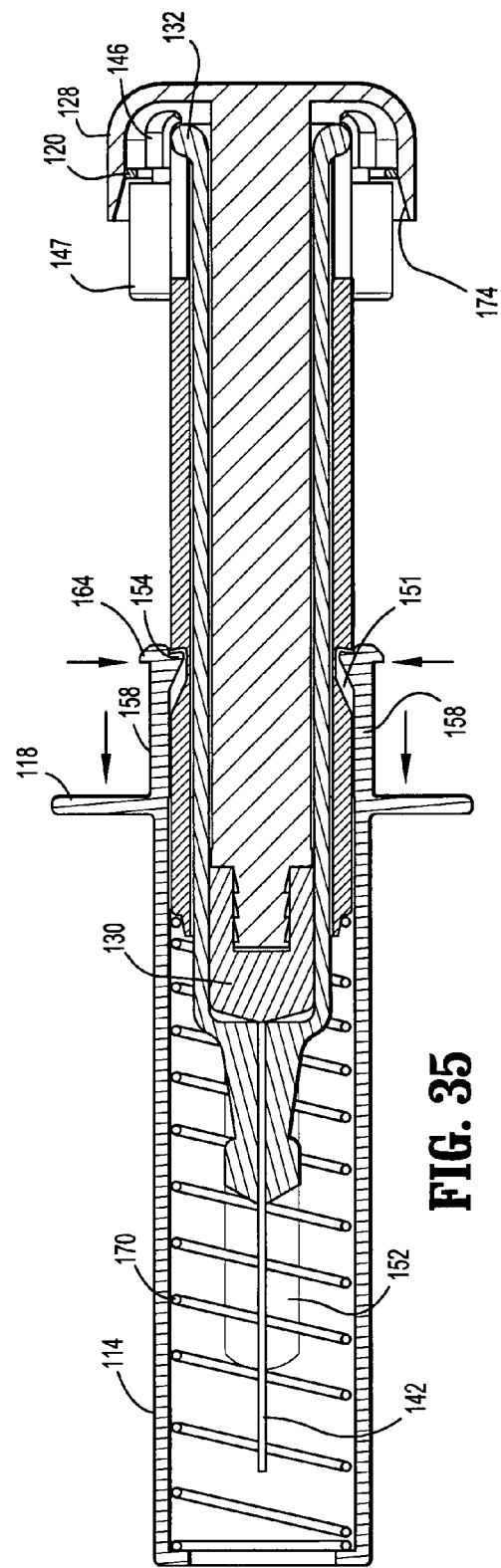

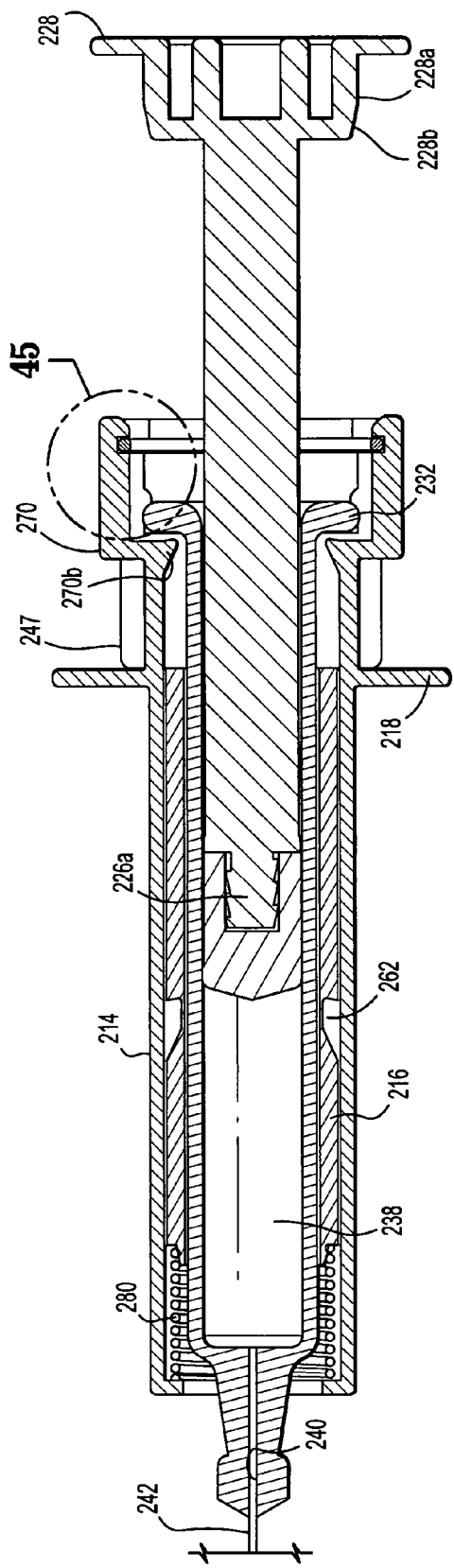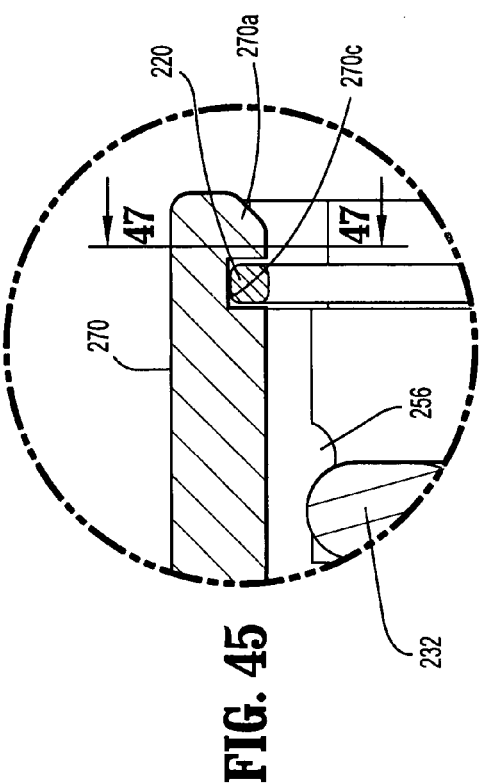
FIG. 44
FIG. 45

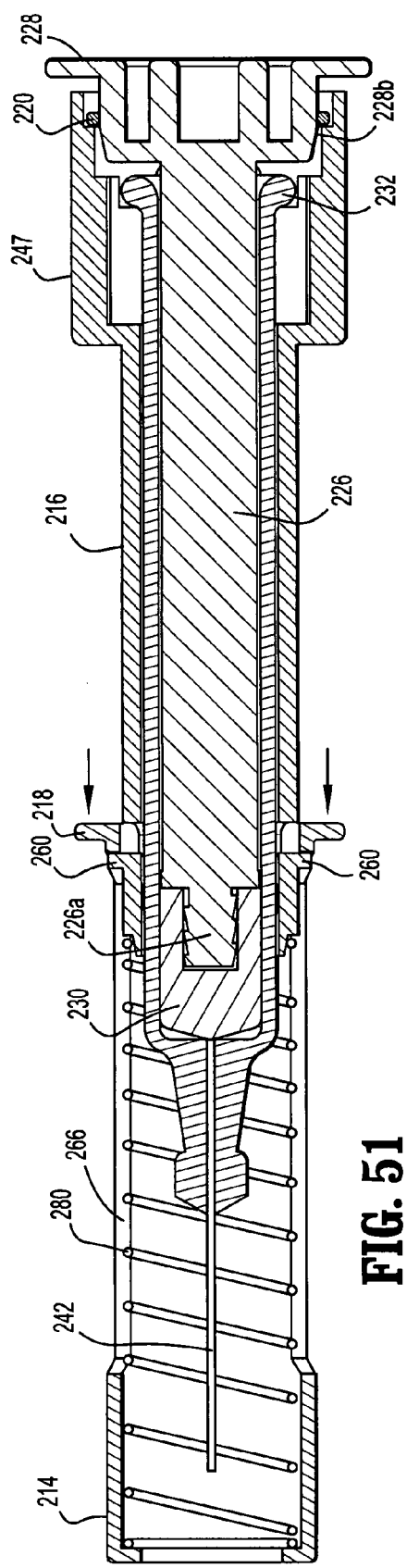
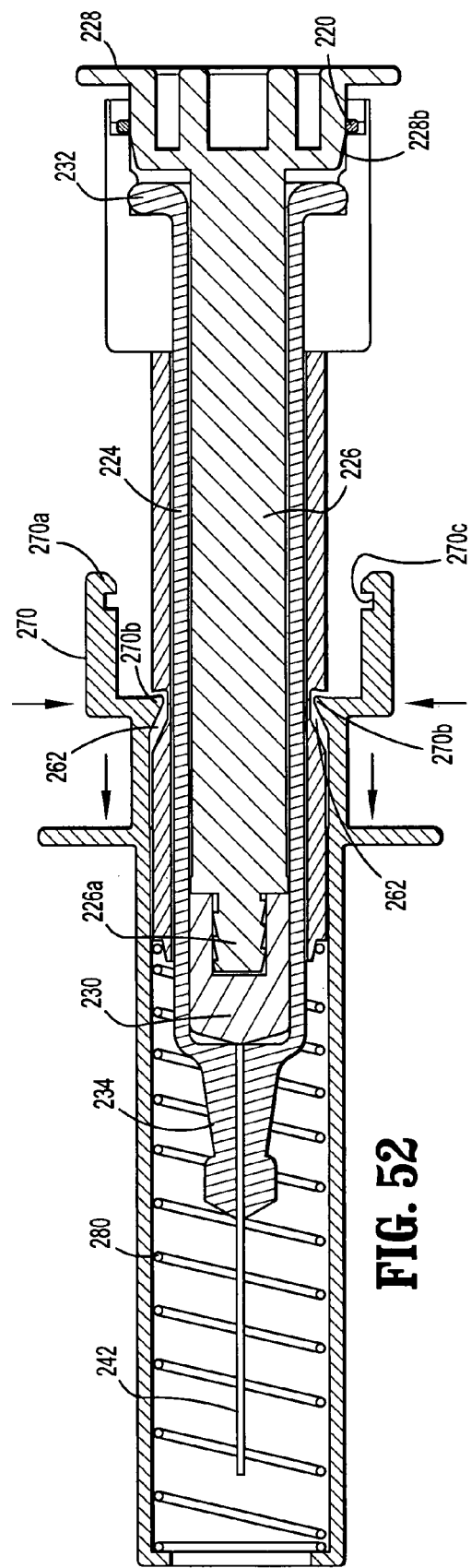
FIG. 51
FIG. 52

PASSIVE LATCH RING SAFETY SHIELD FOR INJECTION DEVICES

CROSS-REFERENCE TO RELATED APPLICATIONS

This application claims priority to U.S. Provisional Application Ser. No. 60/784,558, filed Mar. 21, 2006 and U.S. Provisional Application Ser. No. 60/848,205, filed Sep. 29, 2006, the entire contents of which is incorporated herein by reference.

TECHNICAL FIELD

The present disclosure relates to a safety shield for use with injection devices. More specifically, the present disclosure relates to a passive safety shield for use with medical injection devices, e.g., prefilled syringes, which moves from a retracted position to an extended position in response to actuation of a plunger of the medical injection device.

BACKGROUND OF RELATE ART

Safety shields for shielding needles of medical devices are well known in the art. Safety shields minimize the risks associated with inadvertent needle stick injuries which subject doctors, nurses and medical personnel to exposure to HIV, hepatitis and other serious blood-borne pathogens.

Passively activated safety shield devices are also known in the art. Typically, such devices actuate the safety shield in response to normal usage of a medical device to which the safety shield device is attached, e.g., actuation of a plunger assembly of the medical device. Such devices tend to be overly complex and expensive to manufacture.

Accordingly, a continuing need exists in the art for a passively actuated safety shield for use with a medical device which is of less complexity than known devices and can be inexpensively manufactured.

SUMMARY

In accordance with the present disclosure, a passive safety shield device is disclosed which includes an inner sheath having a proximal end and a distal end. The inner sheath defines a longitudinal channel which extends between the proximal and distal ends and is dimensioned to receive an injection device. An outer sheath has a proximal end and a distal end and defines a longitudinal channel which is dimensioned to slidably receive the inner sheath. A biasing member is supported within the outer sheath and is positioned to urge the outer sheath from a retracted position to an advanced position in relation to the inner sheath. A deformable ring is positioned on the safety shield device and is deformable from an undeformed condition to a deformed condition. The deformable ring in its undeformed condition is configured to retain the outer sheath in the retracted position. The deformable ring is positioned to be deformed to a deformed condition in response to actuation of an injection device, wherein in its deformed condition, the deformable ring is no longer configured to retain the outer sheath in the retracted position.

In one embodiment, the deformable ring is supported on the outer sheath and is positioned to abut a shoulder on the inner sheath in its undeformed condition to retain the outer sheath in the retracted position. The deformable ring can be supported within an annular recess formed about a proximal end of the outer sheath. The annular recess can include at least one opening and the deformable ring can include at least one projection which is slidably received in the at least one opening. In one embodiment, the at least one opening includes a plurality of openings and the at least one projection includes a plurality of projections.

In one embodiment, the deformable ring is substantially oval in its undeformed condition and substantially circular in its deformed condition.

In one embodiment, the inner sheath includes a cutout positioned to receive the deformable ring when the outer sheath is in the advanced position to retain the outer sheath in the advanced position.

A collar having a finger flange can be supported on the outer sheath. The finger flange facilitates grasping and actuation of the safety shield and injection device by medical personnel.

The inner sheath can include at least one engagement member configured to engage an injection device to secure the inner sheath to the injection device. In one embodiment, the at least one engagement member includes a flexible arm having an engaging portion configured to engage a portion of the injection device. The at least one engagement member can include first and second diametrically opposed engagement members.

In one embodiment, the outer sheath includes at least one guide channel dimensioned to slidably receive at least one longitudinal rib formed on the inner sheath to guide the outer sheath between the retracted and advanced positions and to prevent rotation of the outer sheath in relation to the inner sheath. The at least one guide channel can include a pair of guide channels and the at least one longitudinal rib can include a pair of longitudinal ribs.

In one embodiment, the injection device includes a barrel portion defining a fluid reservoir, a hub portion supporting a hollow needle, and a plunger assembly including a plunger head. The plunger assembly is movable in relation to the barrel portion from a retracted position to an advanced position. The plunger head can include an extended portion positioned to engage the deformable ring when the plunger assembly nears its advanced position.

In one embodiment, the barrel portion of the injection device includes a proximal flange and the inner sheath includes at least one engagement member positioned to engage the proximal flange to mount the inner sheath about the injection device. The at least one engagement member can include a pair of diametrically opposed flexible arms. Each of the arms can include a hook portion positioned to snap over and engage the proximal flange of the barrel portion of the injection device.

BRIEF DESCRIPTION OF THE DRAWINGS

Various embodiments of the presently disclosed passive latch ring safety shield and injection device assembly are disclosed herein with reference to the drawings, wherein:

FIG. 1 is a perspective view from the proximal end of one embodiment of the presently disclosed passive latch ring safety shield mounted on an injection device;

FIG. 2 is a perspective view of the passive latch ring safety shield and injection device shown in FIG. 1;

FIG. 9 is a cross-sectional view taken along section lines 9-9 of FIG. 6;

FIG. 10 is an enlarged view of the indicated area of detail shown in FIG. 9;

FIG. 16 is a cross-sectional view as shown in FIG. 14 as the outer sheath moves from the retracted position towards the advanced position;

FIG. 17 is a cross-sectional view as shown in FIG. 16 with the outer sheath in the fully advanced position;

FIG. 19 is a perspective view from the proximal end of another embodiment of the presently disclosed passive latch ring safety shield mounted on an injection device;

FIG. 20 is a perspective view from the distal end of the passive latch ring safety shield and injection device shown in FIG. 19;

FIG. 27 is a cross-sectional view taken along section lines 19-19 of FIG. 19;

FIG. 28 is an enlarged view of the indicated area of detail shown in FIG. 27;

FIG. 31 is a cross-sectional view taken through a central axis of the passive latch ring safety shield and injection device shown in FIG. 27 ninety degrees offset from the fingers of the outer sheath with the plunger assembly in an advanced position and the outer sheath in a retracted position;

FIG. 32 is a cross-sectional view taken through a central axis of the passive latch ring safety shield and injection device rotated ninety-degrees offset from the sectional view shown in FIG. 31;

FIG. 34 is a cross-sectional view as shown in FIG. 31 with the outer sheath in the fully advanced position;

FIG. 35 is a cross-sectional view as shown in FIG. 32 with the outer sheath in the fully advanced position;

FIG. 44 is a cross-sectional view taken along section lines 44-44 of FIG. 37;

FIG. 45 is an enlarged view of the indicated area of detail shown in FIG. 44;

FIG. 51 is the cross-sectional view shown in FIG. 48 with the outer sheath moved to its advanced position;

FIG. 52 is the cross-sectional view shown in FIG. 49 with the outer sheath moved to its advanced position.

DETAILED DESCRIPTION OF THE EMBODIMENTS

Figure 3:
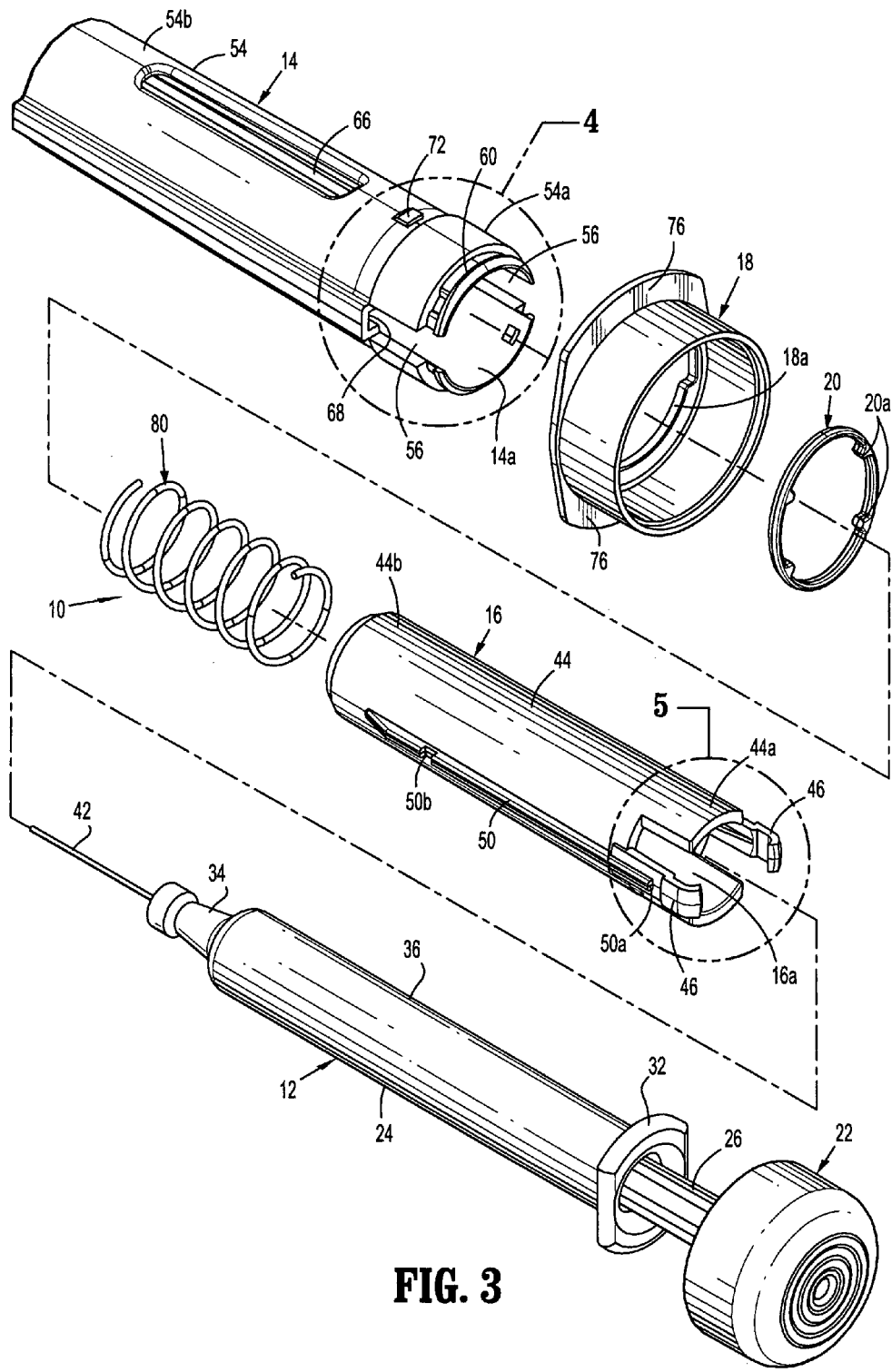
FIG. 3 is a perspective view with parts separated of the passive latch ring safety shield and injection device shown in FIG. 1.

Embodiments of the presently disclosed passive latch ring safety shield assembly for use with an injection device will now be described in detail with reference to the drawings wherein like reference numerals designate identical or corresponding elements in each of the several views.

In this description, the term proximal is generally used to indicate relative nearness of a referenced item to a user of the device and the term distal is used to indicate relative remoteness of a referenced item to a user of the device.

FIGS. 1 and 2 illustrate perspective views of one embodiment the presently disclosed passive latch ring safety shield assembly ("shield assembly") shown generally as 10 mounted on an injection device 12, e.g., a prefilled syringe. Referring also to FIG. 3, briefly, shield assembly 10 includes an outer sheath 14, an inner sheath 16, a collar 18 and a latch ring 20. Outer sheath 14 defines a longitudinal channel or through bore 14a which is dimensioned to slidably receive inner sheath 16. Inner sheath 16 also defines a longitudinal channel or throughbore 16a which is dimensioned to receive injection device 12 as will be discussed in further detail below. Although outer sheath 14 and inner sheath 16 are shown as being substantially cylindrical, other configurations are envisioned, e.g., rectangular, oval, etc.

Figure 6:
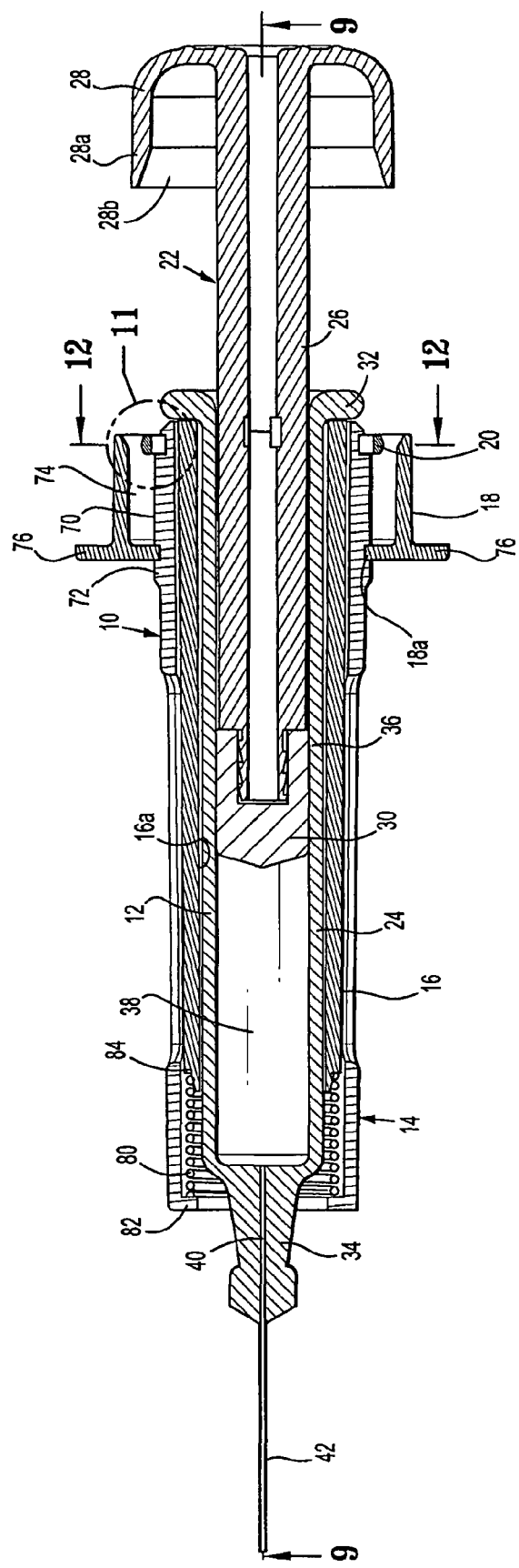
FIG. 6 is a cross-sectional view taken along section lines 6-6 of FIG. 1.
Figure 7:
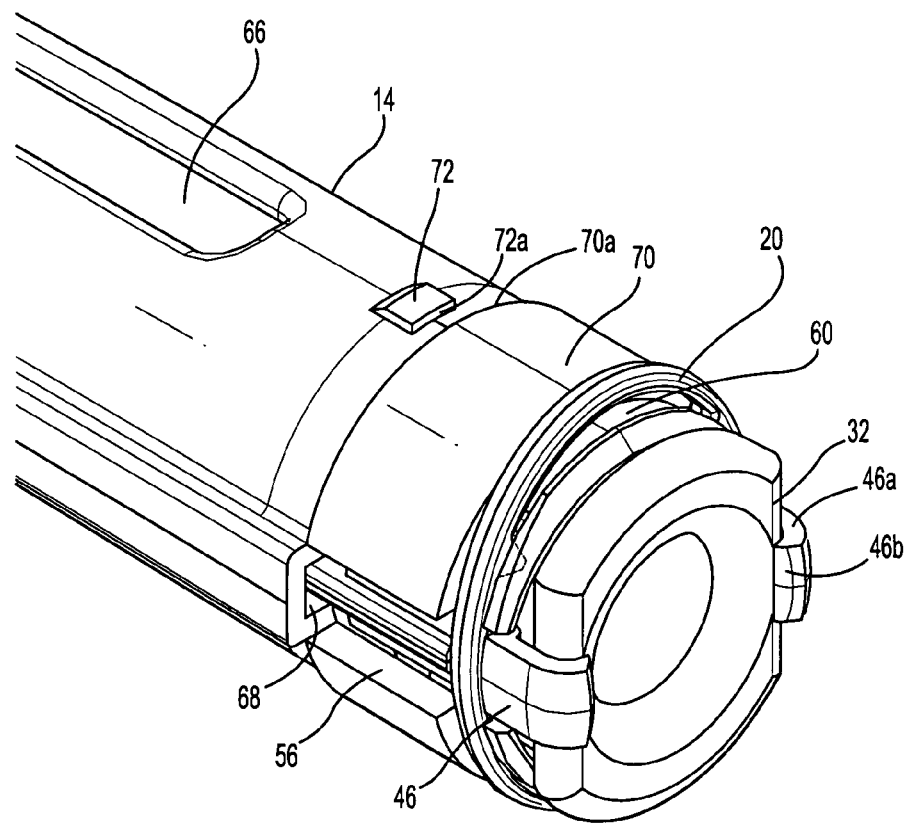
FIG. 7 is a perspective view of the proximal end of the passive latch ring safety shield and injection device shown in FIG. 1 with the plunger assembly removed.
Figure 8:
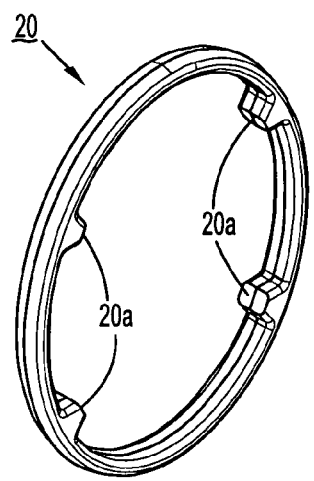
FIG. 8 is a side perspective view of the latch ring of the passive latch ring safety shield shown in FIG. 1.
Figure 11:
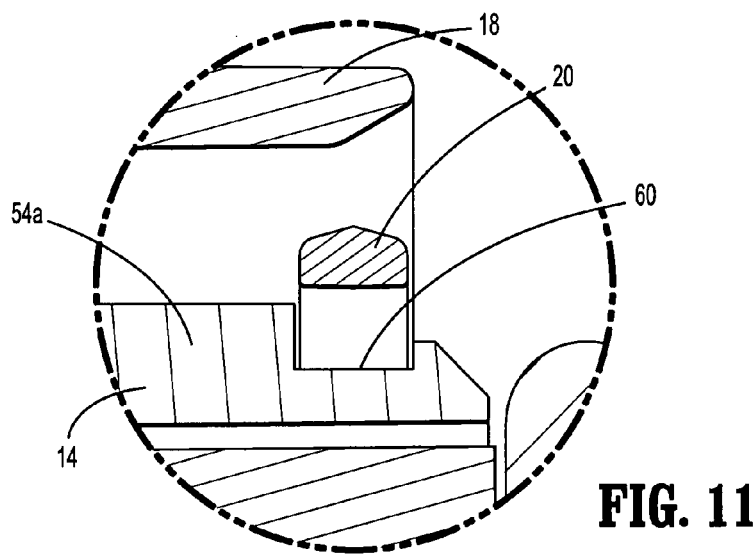
FIG. 11 is an enlarged view of the indicated area of detail shown in FIG. 6.

Referring also to FIG. 6, injection device 12 includes a plunger assembly 22 and a syringe body 24. Plunger assembly 22 includes a plunger rod 26, a head 28 formed on a proximal end of plunger rod 26 and a plunger 30 supported on a distal end of plunger rod 26. In one embodiment, plunger rod 26 and head 28 are integrally formed and plunger 30 is pressed onto a reduced diameter portion 26a of plunger rod 26. Alternately, other plunger assembly configurations are envisioned.

Syringe body 24 includes a proximal flange member 32, a distal hub portion 34, and a central barrel portion 36. Barrel portion 36 defines a fluid reservoir 38 (FIG. 6) and is dimensioned to be received within longitudinal channel 16a of inner sheath 16. Hub portion 34 defines a bore 40 which receives and supports a hollow needle 42. Bore 40 fluidly connects fluid reservoir 38 with hollow needle 42. In one embodiment, proximal flange member 32 defines a truncated disc which is engageable by a portion of inner sheath 16, as will be discussed in further detail below, to secure injection device 12 within channel 16a of inner sheath 16.

Figure 5:
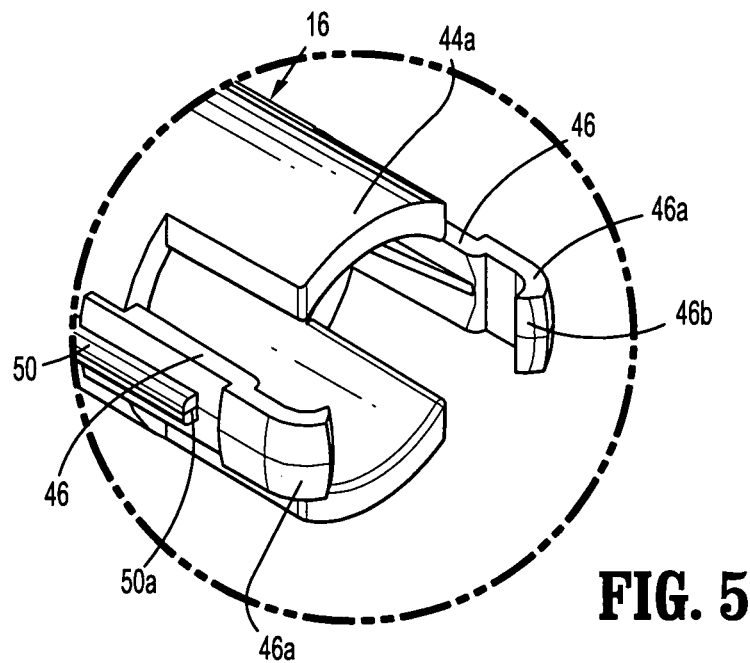
FIG. 5 is an enlarged view of the indicated area of detail shown in FIG. 3.

Referring to FIGS. 3, 5 and 9, inner sheath 16 includes a tubular body 44 having a proximal end 44a and a distal end 44b. In one embodiment, a pair of diametrically opposed, cantilevered arms 46 extend proximally from proximal end 44a of body 44 of inner sheath 16. Each of arms 46 has a degree of flexibility and includes an inwardly extending hook or engaging portion 46a. A proximal surface 46b of each hook portion 46a is tapered. When barrel portion 36 of injection device 12 is slid into channel 16a of inner sheath 16, proximal surfaces 46b of flexible arms 46 engage proximal flange member 32 of injection device 12 to deflect flexible arms 46 outwardly. As arms 46 flex outwardly, engaging portions 46a of arms 46 snap over and hook proximal flange member 32 of syringe body 24 to secure syringe body 24 within inner sheath 16 (see FIG. 9). Although two diametrically opposed flexible arms are illustrated, it is envisioned that one or more randomly positioned flexible arms may be used.

A pair of longitudinally extending ribs 50 are positioned on diametrically opposed sides and along a substantial portion of the length of inner sheath 16. Each of ribs 50 includes a proximal shoulder 50a and a distal cutout 50b. Proximal shoulder 50a (FIG. 5) and distal cutout 50b are dimensioned and positioned to receive a portion of latch ring 20, as will be discussed in further detail below, to secure outer sheath 14 in its retracted and advanced positions, respectively. Alternately, one or more ribs may be provided.

Referring to FIGS. 3, 4, 6 and 9, outer sheath 14 includes a tubular body 54 having a proximal end 54a and a distal end 54b. Proximal end 54a, best shown in FIG. 4, includes a pair of cutouts 56 and an annular recessed channel 60. Cutouts 56 are dimensioned to receive cantilevered arms 46 of inner sheath 16. Annular channel 60 is dimensioned to receive latch ring 20 therein and includes four spaced openings 62 formed in a base of channel 60. Openings 62 are dimensioned to slidably receive inwardly extending projections 20a formed along an inner wall of latch ring 20 such that latch ring 20 is non-rotatably retained within annular channel 60. It is envisioned that one or more openings and projections may be provided.

Body 54 also includes a pair of diametrically opposed longitudinal slots 66 (FIG. 3) and a pair of elongated diametrically opposed longitudinally extending guide channels 68. Each guide channel 68 is positioned to receive a longitudinal rib 50 of inner sheath 16. When rib 50 is positioned within guide channel 68, inner sheath 16 is prevented from rotating within outer sheath 16. Guide channel 68 also functions to guide movement of outer sheath 14 about inner sheath 16 during movement of outer sheath 14 from its retracted position to its advanced position. Longitudinal slots 66 enhance visualization of fluid reservoir 38 within inner sheath 16 when outer sheath 14 is in its retracted position.

Figure 4:
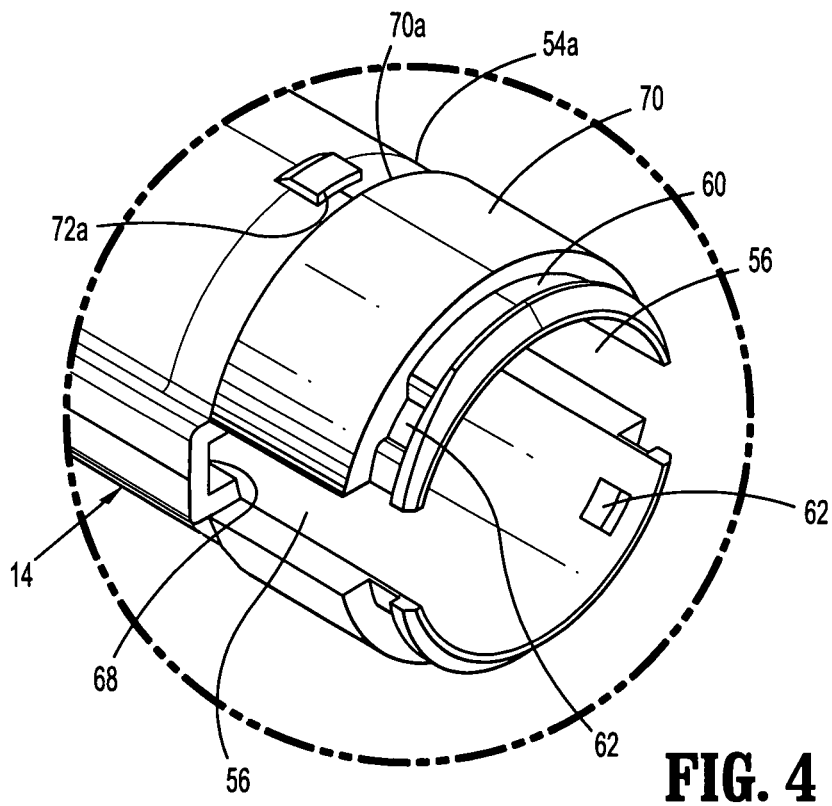
FIG. 4 is an enlarged view of the indicated area of detail shown in FIG. 3.

Referring to FIGS. 3, 4 and 6, body 54 of outer sheath 14 includes an increased diameter portion 70 positioned on a proximal end 54a thereof. Increased diameter portion 70 defines a distally facing shoulder 70a (FIG. 4). A pair of diametrically opposed tabs 72, each including a proximally facing shoulder 72a, are positioned on body 54 at a position distal of increased diameter portion 70. The space between shoulder 70a of increased diameter portion 70 and shoulders 72a of tabs 72 is dimensioned to receive collar 18. More specifically, collar 18 is substantially cylindrical and includes an inwardly extending annular flange 18a which is slid over proximal end 54a of outer sheath 14 and snap fit into the space between shoulder 70a of increased diameter portion 70 and shoulders 72a of tabs 72. As illustrated in FIG. 6, collar 18 defines an annular recess 74 with an outer surface of outer sheath 14. Annular recess 74 is dimensioned to receive distally extending portion 28a of head 28 of plunger assembly 22 when plunger assembly 22 is moved to its advanced position. Distally extending portion 28a includes an angled distal face 28b which is positioned to engage latch ring 20 when plunger assembly 22 nears its advanced position as will be discussed in further detail below.

Collar 18 also includes one or more finger flanges 76 which extend radially outwardly from outer sheath 14. Finger flanges 76 define gripping surfaces to facilitate actuation of plunger assembly 22 as will be discussed in further detail below.

Figure 12:
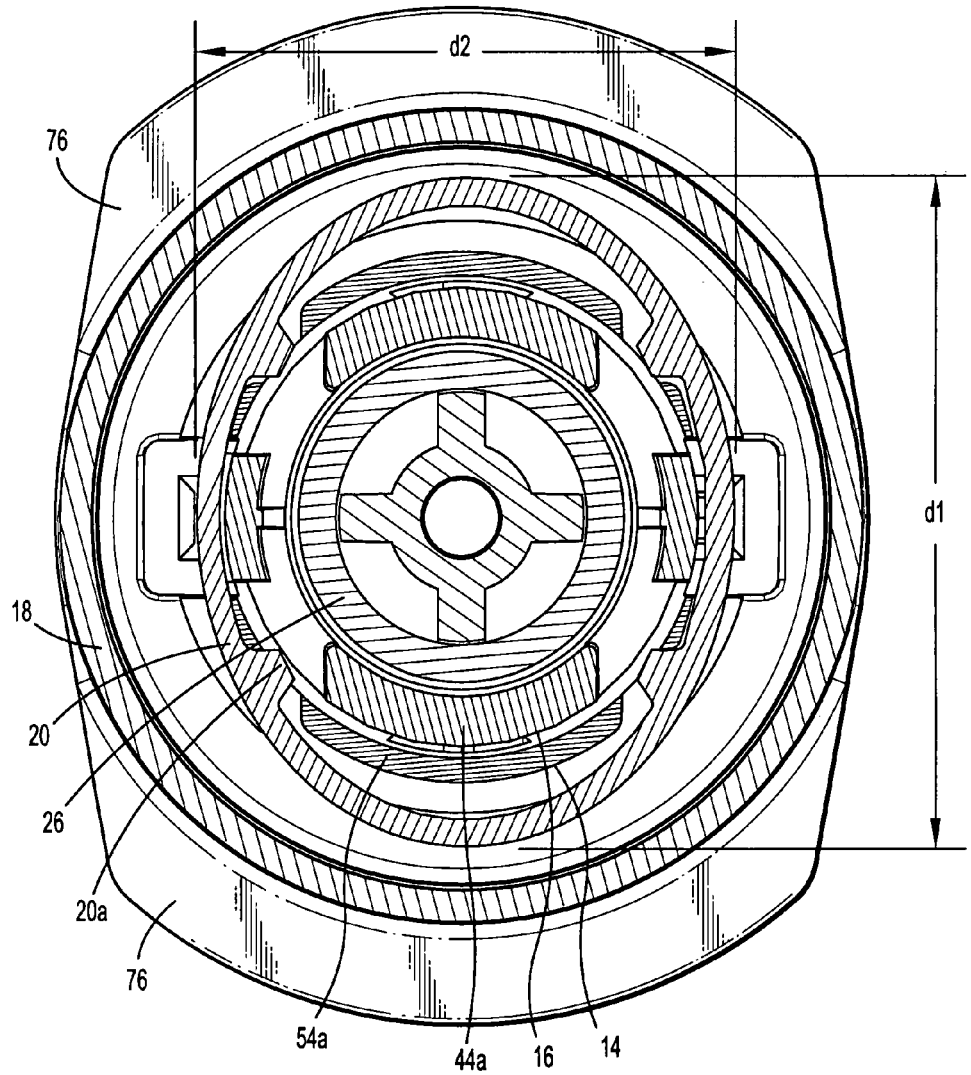
FIG. 12 is a cross-sectional view taken along section lines 12-12 of FIG. 6.

Referring to FIGS. 3 and 7-12, latch ring 20 is substantially resilient and defines an undeformed oval configuration. As discussed above, latch ring 20 is supported in annular recessed channel 60 at proximal end 54a of body 54 of outer sheath 14. As best seen in FIG. 12, latch ring 20 defines a major diameter d1 and a minor diameter d2. The portion of latch ring 20 defining major diameter d1 of latch ring 20 bows outwardly from annular channel 60 (see FIG. 11). However, the portion of latch ring 20 which defines minor diameter d2 is positioned within annular channel 60 and extends through cutouts 56 of outer sheath 14 into engagement with proximal shoulder 50a of longitudinal ribs 50 of inner sheath 16 when outer sheath 14 is in its retracted position. See FIG. 10. Since latch ring 20 is secured to outer sheath 14 via projections 20a, the positioning of latch ring 20 against proximal shoulders 50a of ribs 50 of inner sheath 16 prevents longitudinal movement of outer sheath 14 in relation to inner sheath 16. Thus, latch ring 20 retains outer sheath 14 in its retracted position.

Referring again to FIGS. 3 and 6, a biasing member, e.g., coil spring 80, is positioned between an inner radially extending distal wall 82 of outer sheath 14 and a distal end surface 84 of inner sheath 16. When outer sheath 14 is in its retracted position, coil spring 80 is compressed to urge outer sheath 14 towards its advanced positioned. As discussed above, when latch ring 20 is positioned in abutment with proximal shoulder 50a of longitudinal rib 50 of inner sheath 16, outer sheath 14 is retained in its retracted position.

Figure 13:
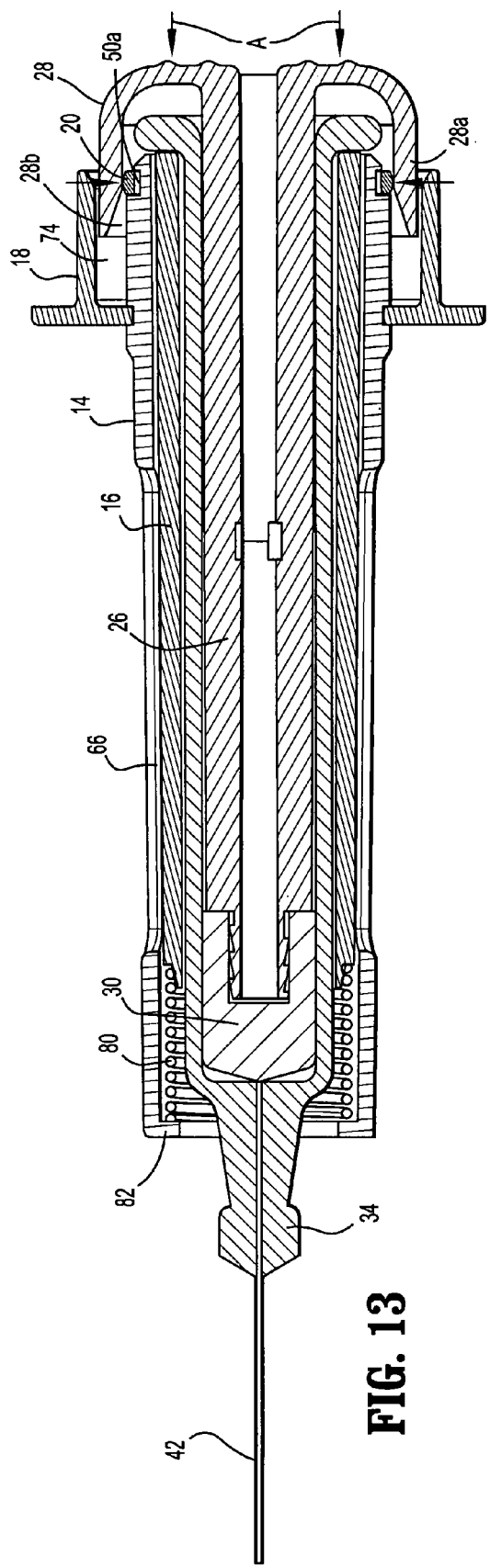
FIG. 13 is a cross-sectional view taken through a central axis of the passive latch ring safety shield and injection device shown in FIG. 9 ninety degrees offset from the cantilevered arms of the inner sheath with the plunger assembly in an advanced position and the outer sheath is in a retracted position.
Figure 14:
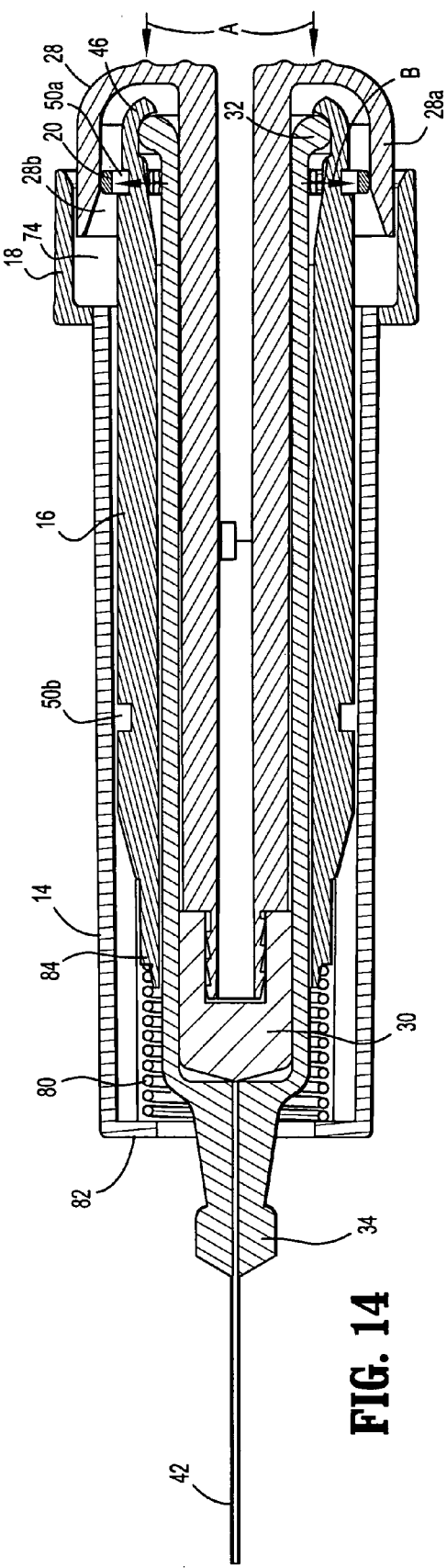
FIG. 14 is a cross-sectional view taken through a central axis of the passive latch ring safety shield and injection device ninety-degrees offset from the sectional view shown in FIG. 13.
Figure 15:
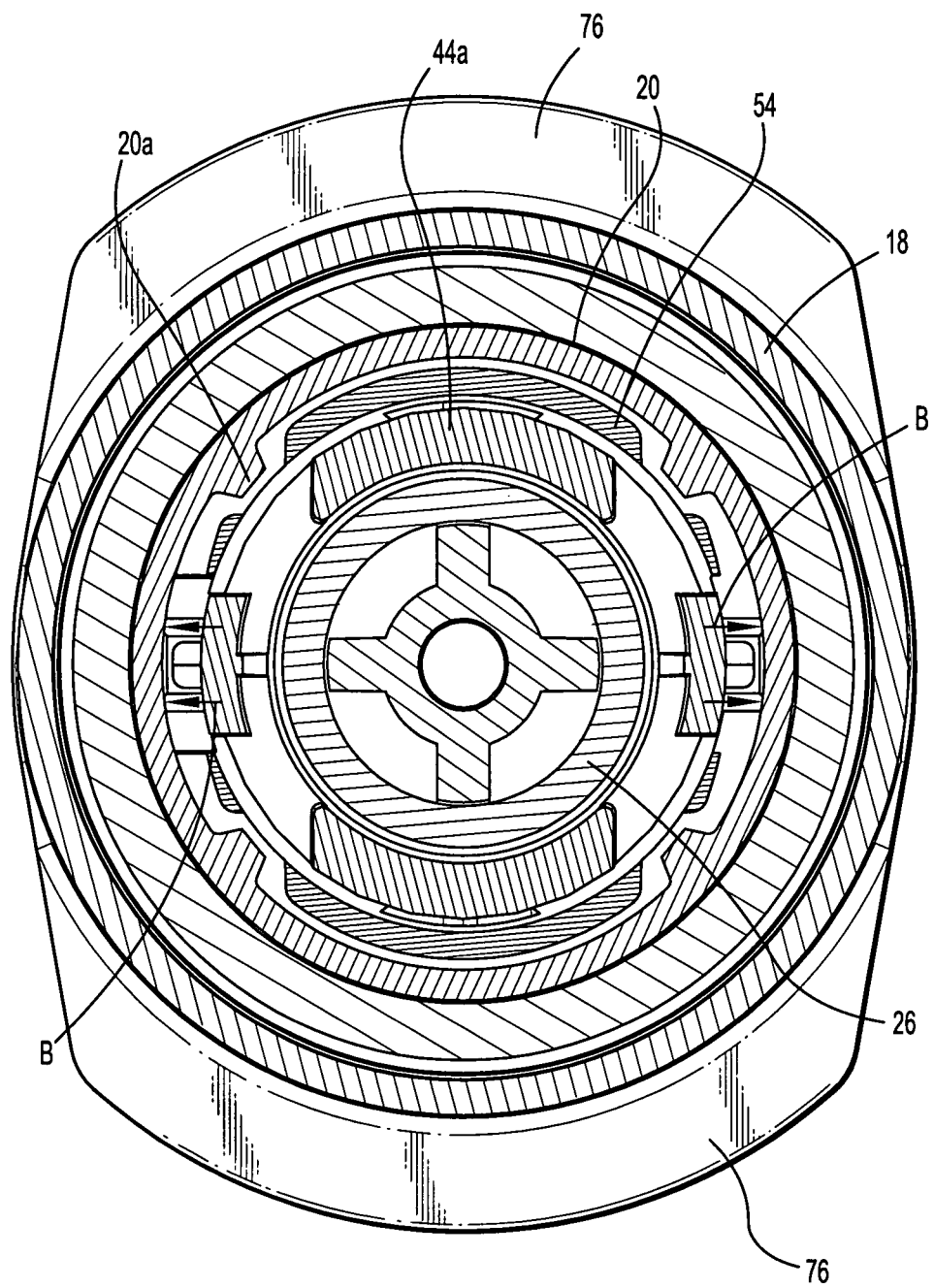
FIG. 15 is a cross-sectional view taken along section lines 12-12 of FIG. 6 after the plunger assembly has been moved to the advanced position.

Referring to FIGS. 13-15, when plunger assembly 22 is actuated by a doctor, nurse or other medical personnel, i.e., advanced in the direction indicated by arrow "A" in FIGS. 13 and 14, as distally extending portion 28a of plunger head begins to enter annular recess 74, angled face 28b of plunger head 28 engages the portion of latch ring 20 defining major diameter d1 (FIG. 12) to urge major diameter portion d1 inwardly. As a result, minor diameter portion d2 of latch ring 20 moves outwardly as latch ring 20 is deformed by distally extending portion 28a of plunger head 28 to move latch ring 20 in the direction indicated by arrow B in FIG. 15 out of engagement with proximal shoulder 50a of rib 50 of inner sheath 16. It is noted that although latch ring 20 no longer retains outer sheath 14 in its retracted position, outer sheath 14 will not immediately be moved by coil spring 80 to its advanced position until finger flanges 76 are released by medical personnel.

Figure 18:
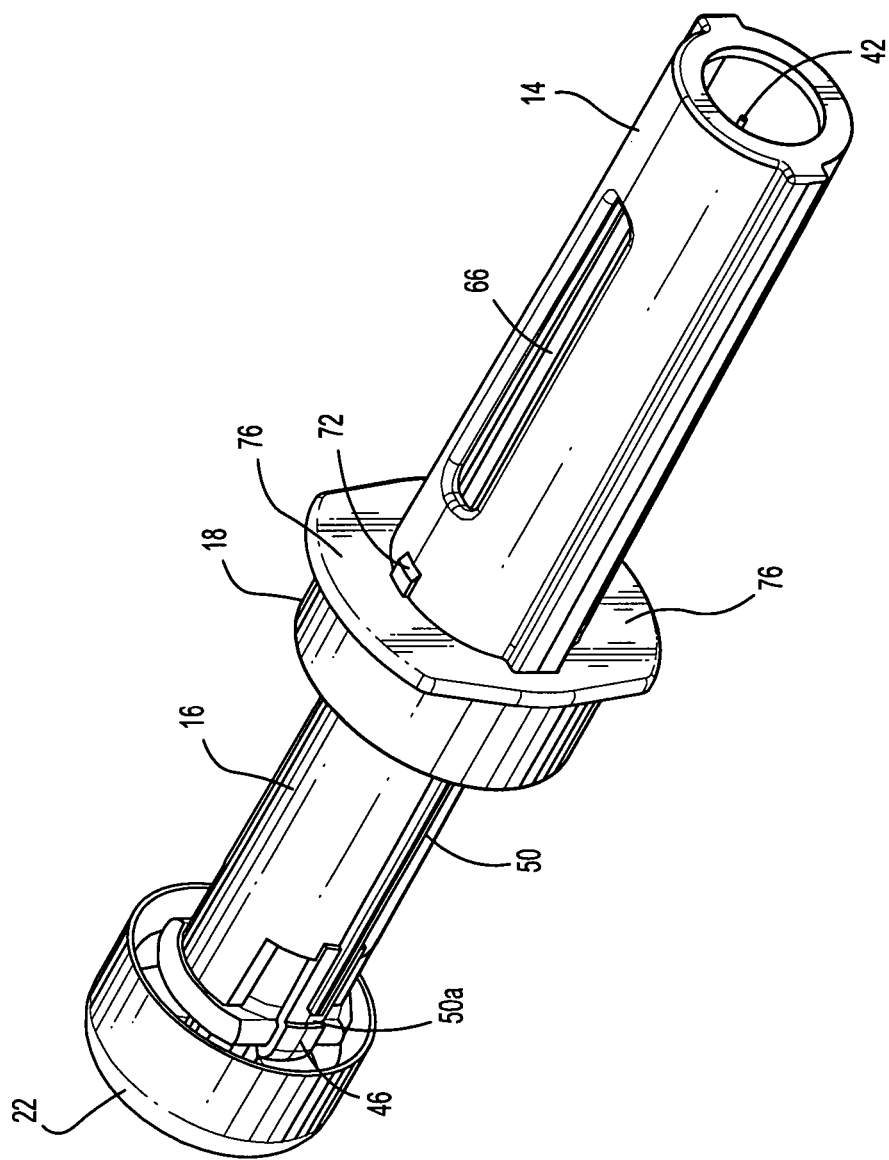
FIG. 18 is a side perspective view of the passive latch ring safety shield and injection device shown in FIG. 1 with the plunger assembly and the outer sheath in the advanced position.

Referring to FIGS. 16-18, when finger flanges 76 (FIG. 18) are released by medical personnel, coil spring 80 urges outer sheath 14 in the direction indicated by arrows "C" in FIGS. 16 and 17 to its advanced position. As illustrated, latch ring 20 moves with outer sheath 14 and slides along an external surface of inner sheath 16 (FIG. 16) until it is received in distal cutouts 50b of longitudinal ribs 50 of inner sheath 16 (FIG. 17). Receipt of latch ring 20 within distal cutouts 50b functions to lock outer sheath 14 in its advanced position located about hollow needle 42.

Figure 21:
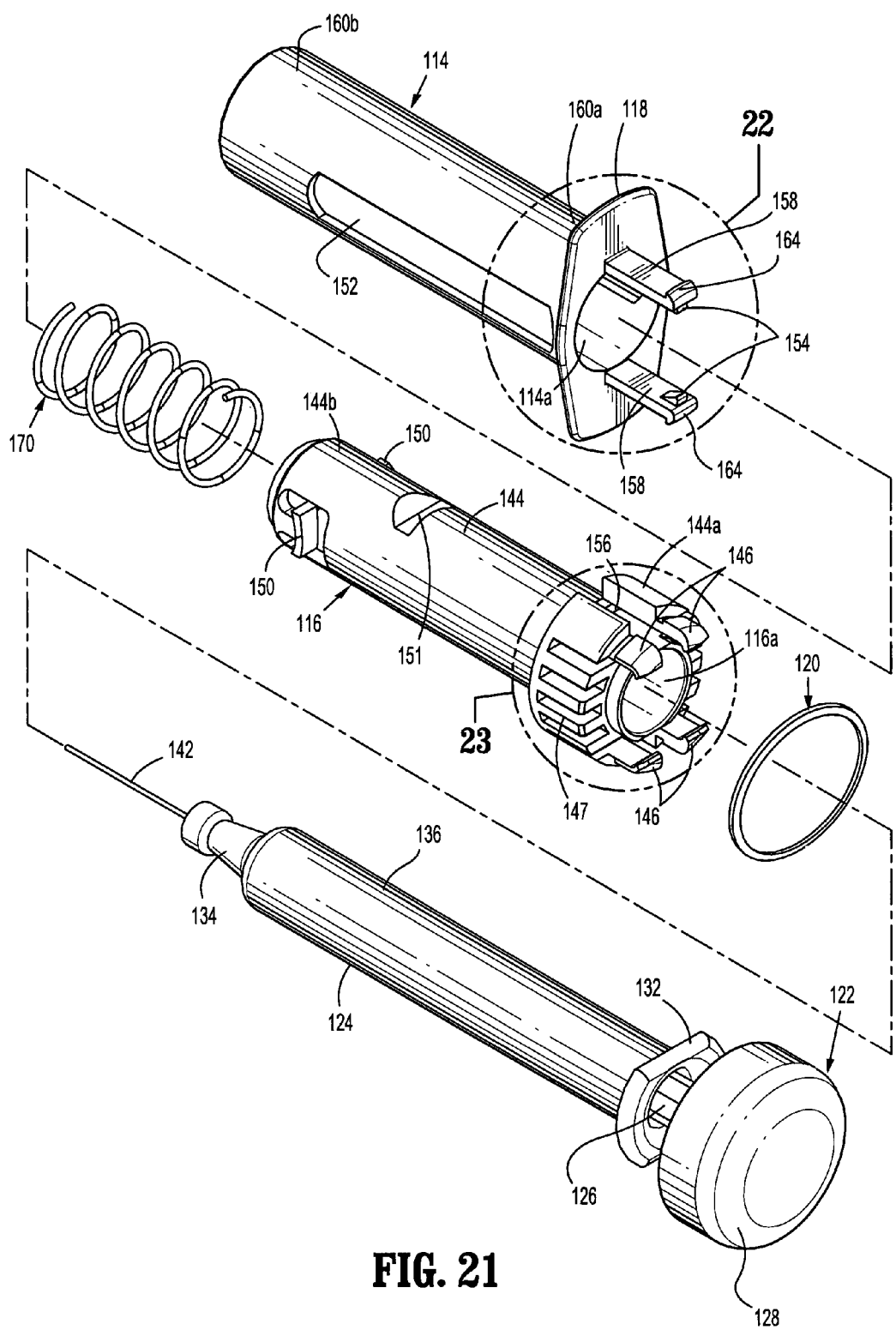
FIG. 21 is a perspective view from the proximal end of the passive latch ring safety shield and injection device shown in FIG. 19 with parts separated.

FIGS. 19 and 20 illustrate perspective views of another embodiment of the presently disclosed passive latch ring safety shield assembly ("shield assembly") shown generally as 100 mounted on an injection device 112, e.g., a prefilled syringe. Referring also to FIG. 21, briefly, shield assembly 100 includes an outer sheath 114, an inner sheath 116, and a latch ring 120. Outer sheath 114 includes a finger flange 118 and defines a longitudinal channel or throughbore 114a which is dimensioned to slidably receive inner sheath 116. Inner sheath 116 also defines a longitudinal channel or throughbore 116a which is dimensioned to receive injection device 112 as will be discussed in further detail below. Although outer sheath 114 and inner sheath 116 are shown as being substantially cylindrical, other configurations are envisioned.

Figure 24:
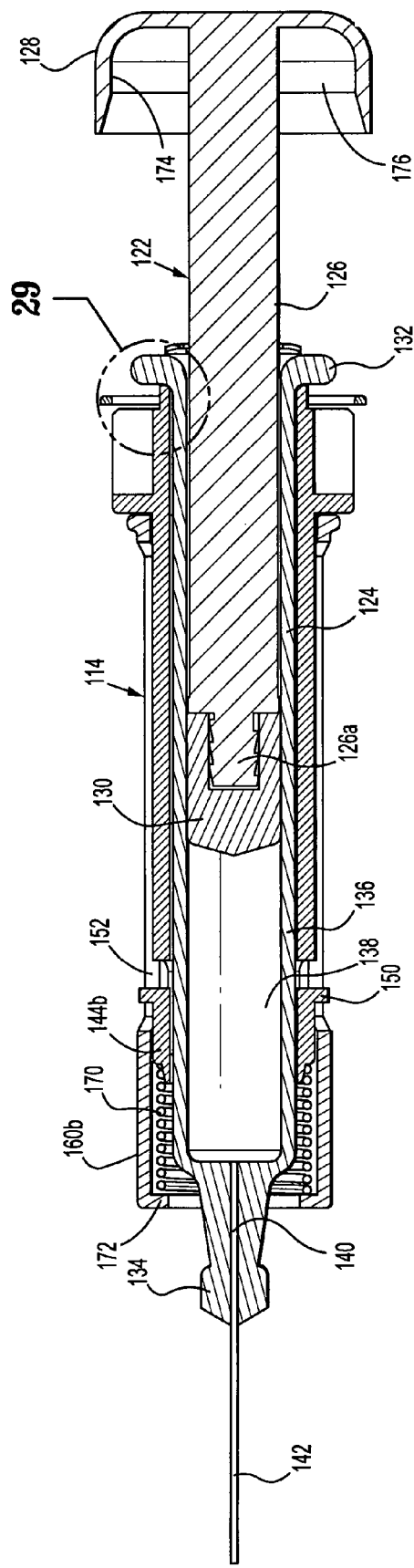
FIG. 24 is a cross-sectional view taken along section lines 24-24 of FIG. 19.

Referring also to FIG. 24, injection device 112 includes a plunger assembly 122 and a syringe body 124. Plunger assembly 122 includes a plunger rod 126, a head 128 formed on a proximal end of plunger rod 126 and a plunger 130 supported on a distal end of plunger rod 126. In one embodiment, plunger rod 126 and head 128 are integrally formed and plunger 130 is pressed onto a reduced diameter portion 126a of plunger rod 126. Alternately, other plunger assembly configurations are envisioned.

Syringe body 124 includes a proximal flange member 132, a distal hub portion 134, and a central barrel portion 136. Barrel portion 136 defines a fluid reservoir 138 (FIG. 24) and is dimensioned to be received within longitudinal channel 116a of inner sheath 116. Hub portion 134 defines a bore 140 which receives and supports a hollow needle 142 such that hollow needle 142 is fluidly connected with fluid reservoir 138 of syringe body 124. In one embodiment, proximal flange member 132 defines a truncated disc which is engageable by a portion of inner sheath 116, as will be discussed in further detail below, to secure injection device 112 within channel 116a of inner sheath 116. Plunger assembly 122 is movable in relation to syringe body 124 from a retracted to an advanced position in a known manner to eject fluid from or withdraw fluid into needle 142.

Referring to FIGS. 21, 23, 25 and 27, inner sheath 116 includes a tubular body 144 having a proximal end 144a and a distal end 144b. In one embodiment, proximal end 144a of inner sheath 116 includes an enlarged head 147 having a plurality of flexible arms 146 which are configured to engage proximal flange member 132 of syringe body 124. More specifically, each of arms 146 include an inwardly extending engaging or hook portion 146a for engaging flange 132 of syringe body 124. Flexible arms 146 also define a recess 146b dimensioned to receive latch ring 120 as will be discussed in further detail below.

When barrel portion 136 of injection device 112 is slid into channel 116a of inner sheath 116, arms 146 engage flange member 132 and are deflected outwardly such that hook portions 146a engage flange member 132. Engagement between arms 146 and flange member 132 secures injection device 112 within longitudinal channel 116a of inner sheath 116 and also prevents rotation of injection device 112 within channel 116a. Although four arms 146 are illustrated, two or more arms can be provided. Alternately other structure for securing injection device 112 within inner sheath 116 can be provided.

Inner sheath 116 also includes diametrically opposed projections 150 formed on its distal end 144b and diametrically opposed cutouts 151 formed between proximal and distal ends 144a and 144b. Projections 150 are dimensioned to be received within elongated slots 152 formed in outer sheath 114 as will be discussed in further detail below. Cutouts 151 are positioned and dimensioned to receive projections 154 on outer sheath 114 to retain outer sheath 114 in its advanced position as will be discussed in further detail below.

As discussed above, proximal end 144a of inner sheath 116 includes an enlarged head 147 which includes flexible arms 146 configured to engage flange member 132 of syringe body 124. Enlarged head 147 also includes a pair of diametrically opposed slots 156. Slots 156 are positioned to slidably receive fingers 158 of outer sheath 114. Fingers 158 extend proximally from outer sheath 114 such that projections 154, which extend inwardly from fingers 158, extend radially inwardly into slots 156. A latch ring 120 is supported within recesses 146b about arms 146 at the proximal end 144a of inner sheath 116. Latch ring 120 extends across slots 146 such that outwardly extending projections 164 of fingers 158 engage latch ring 120 as will be discussed in further detail below.

Outer sheath 114 includes a body 160 having an open proximal end 160a, an open distal end 160b and longitudinal throughbore 114a dimensioned to slidably receive inner sheath 116. In one embodiment, body 160 is substantially cylindrical, although other configurations are envisioned, e.g., rectangular, oval, etc. Slots 152 extend longitudinally along a portion of the length of body 160. Slots 152 are dimensioned to receive projections 150 of inner sheath to prevent rotation of inner sheath 116 in relation to outer sheath 114 while permitting outer sheath 114 to slide longitudinally about inner sheath 116 from a retracted position to an extended or advanced position. Finger flange 118 is formed on the proximal end 160a of outer sheath 114. Finger flange 118 provides a gripping surface for medical personnel operating injection device 112.

Figure 22:
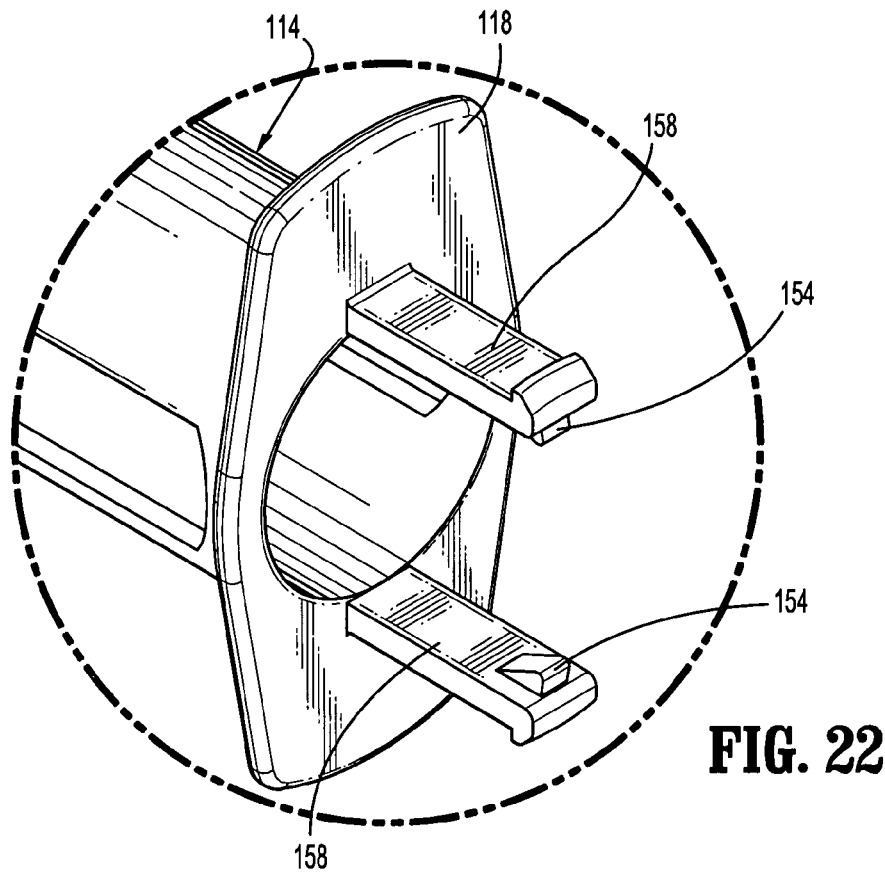
FIG. 22 is an enlarged view of the indicated area of detail shown in FIG. 21.
Figure 23:
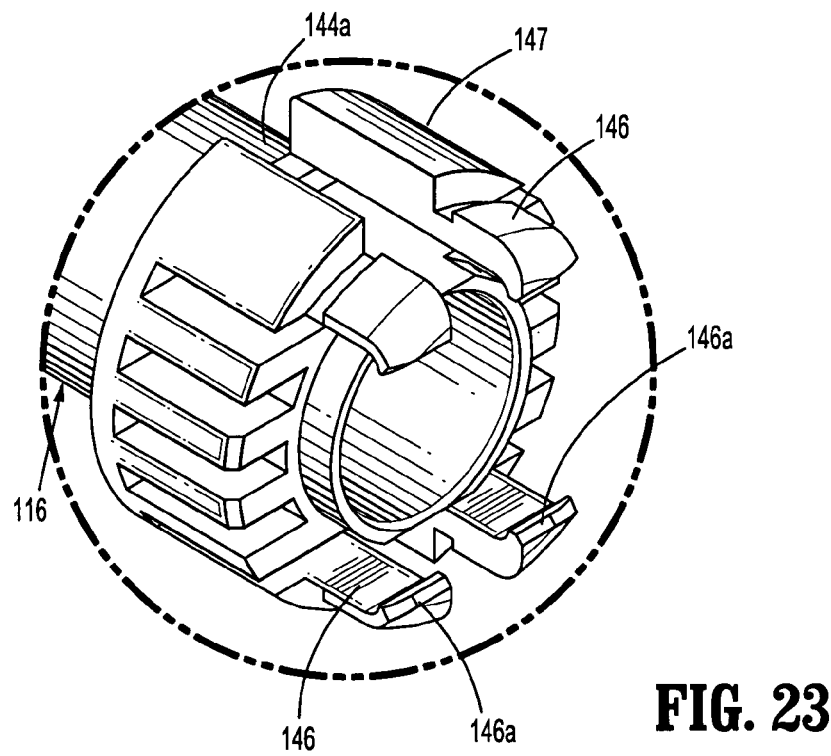
FIG. 23 is an enlarged view of the indicated area of detail shown in FIG. 21.
Figure 25:
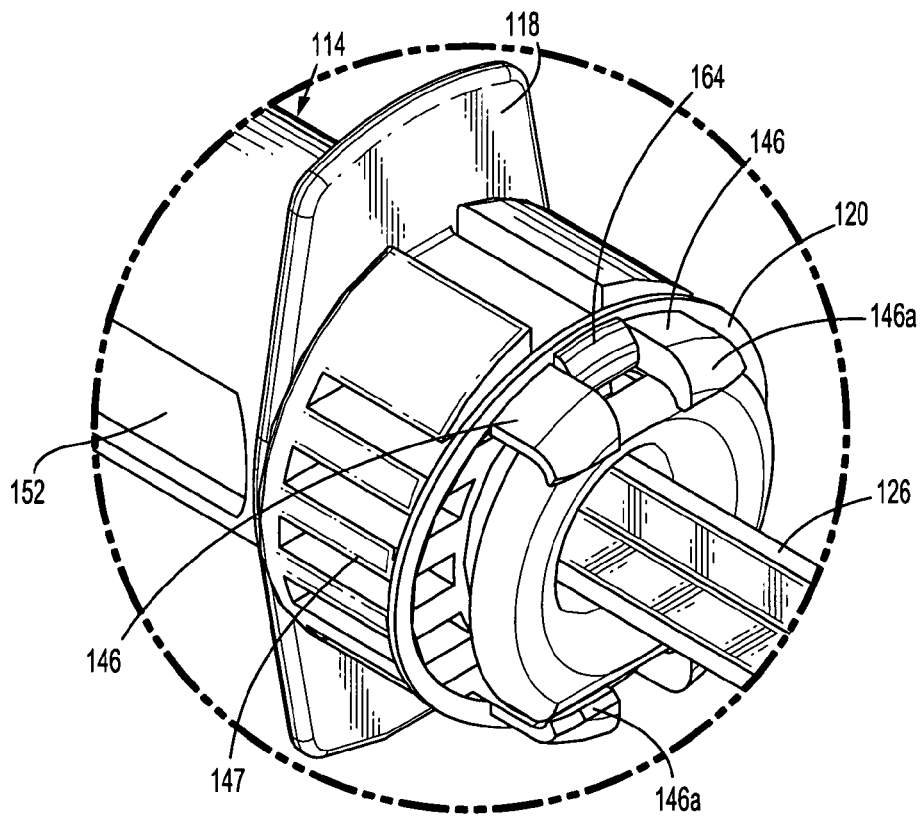
FIG. 25 is an enlarged view of the indicated area of detail shown in FIG. 19.
Figure 26:
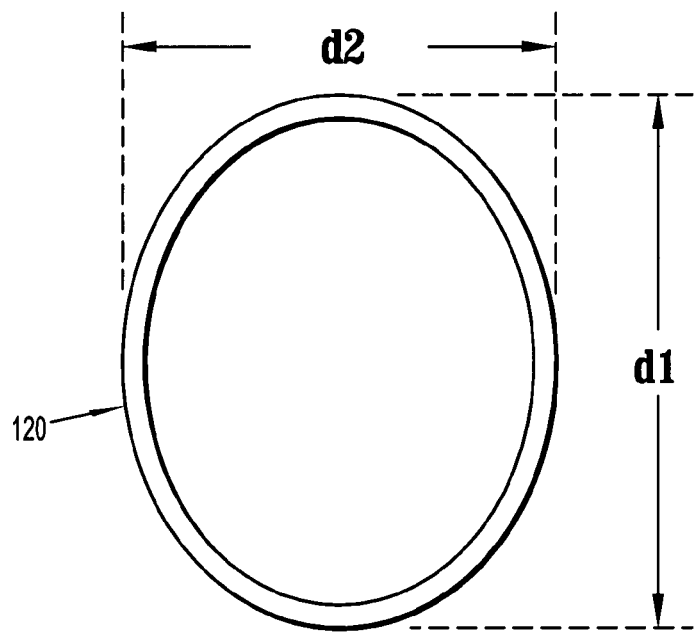
FIG. 26 is a side view of the latch ring of the passive latch ring safety shield shown in FIG. 19.
Figure 29:
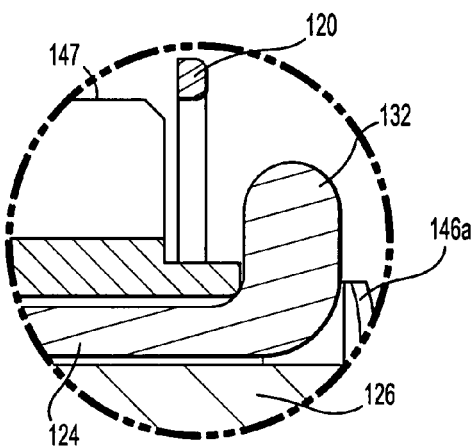
FIG. 29 is an enlarged view of the indicated area of detail shown in FIG. 24.

Referring also to FIGS. 25 and 26, as discussed above, fingers 158 extend from proximal end 160a of outer sheath 114 and include outwardly extending projections 164 (FIG. 22). Latch ring 120 is formed from a flexible material and has an undeformed oval configuration. The undeformed oval configuration defines a major diameter d1 and a minor diameter d2. In its undeformed configuration, projections 164 of fingers 158 engage the portion of latch ring 120 defining minor diameter d2 (FIG. 25) to prevent outer sheath 114 from sliding in relation to inner sheath 116. When latch ring 120 is deformed by plunger assembly 122 during operation of injection device 112, as will be discussed in further detail below, latch ring 120 is deformed into a substantially circular configuration to disengage latch ring 120 from projections 164 and permit outer sheath 114 to slide in relation to inner sheath 116 from a retracted position to an advanced position.

Referring to FIGS. 21 and 24, a biasing member, e.g., a coil spring 170, is positioned within outer sheath 114 between a shoulder 172 formed at distal end 160b of outer sheath 114 and distal end 144b of inner sheath 116. Coil spring 170 urges outer sheath 114 in relation to inner sheath 116 from the retracted position (FIG. 24) to the advanced position (FIG. 33A).

Referring again to FIG. 24, plunger head 128 is substantially cup-shaped and defines an annular recess 176 about plunger rod 126. Annular recess 176 is dimensioned to receive the proximal ends of inner and outer sheaths 116 and 114, respectively, when plunger assembly 122 nears the advanced position, i.e., when plunger assembly 122 is advanced to inject fluid from injection device 112 (see FIG. 31), such that an interior surface 174 of plunger head 128 engages and deforms latch ring 120 from its substantially oval configuration to a substantially circular configuration. As discussed above, when latch ring 120 is deformed, latch ring 120 disengages from projections 164, such that coil spring 170 is able to advance outer sheath 114 in relation to inner sheath 116 from its retracted position to its advanced position.

Figure 30:
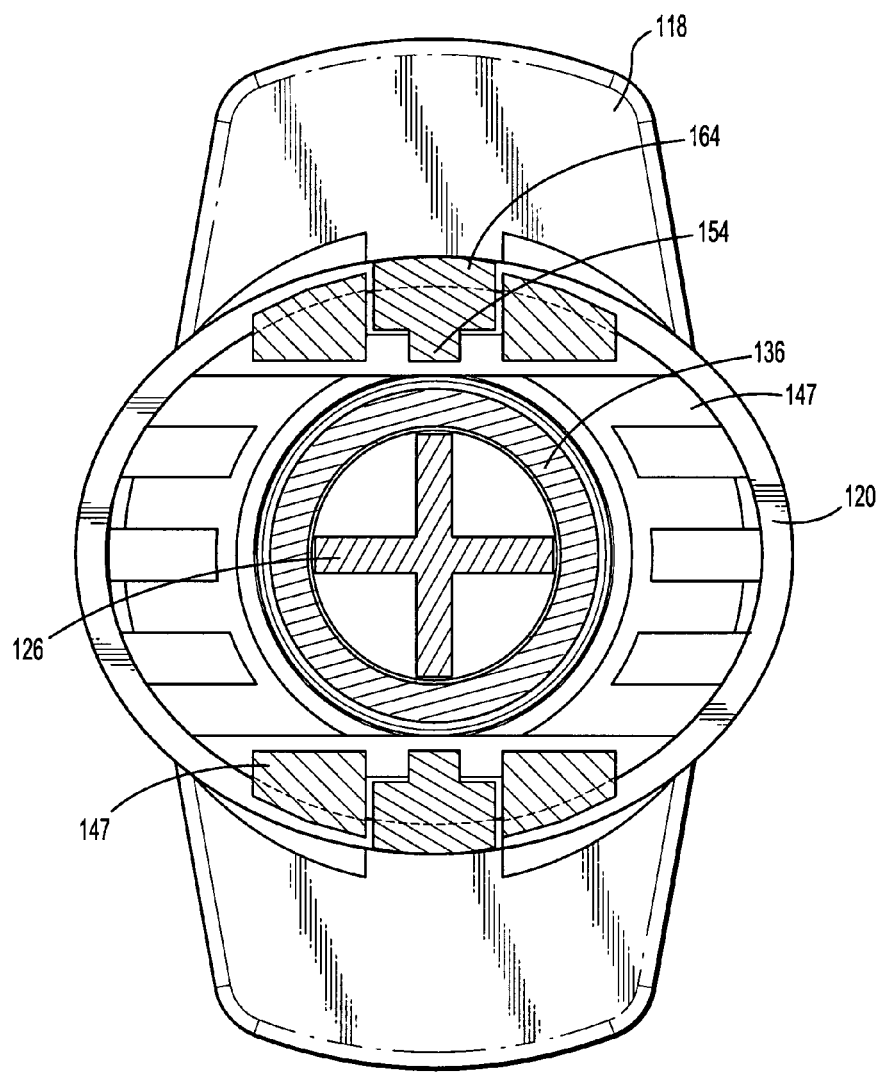
FIG. 30 is a cross-sectional view taken along section lines 28-28 of FIG. 28.

Operation of passive latch ring safety shield assembly 100 will now be described in detail. Referring to FIGS. 27-30, prior to operation of assembly 100, injection device 112 is positioned within inner sheath 116 such that flexible arms 146 of inner sheath 116 engage flange member 132 of injection device 112 to retain injection device 112 within inner sheath 116. Outer sheath 114 is in its retracted position in relation to inner sheath 116 such that hollow needle 142 is exposed. As illustrated in FIGS. 28 and 30, latch ring 120 is engaged by projections 164 such that outer sheath 114 is retained in the retracted position against the bias of coil spring 170. Note also in FIG. 29, that major diameter d1 of latch ring 120 extends radially outwardly of enlarged head 147 of inner sheath 116.

Figure 33:
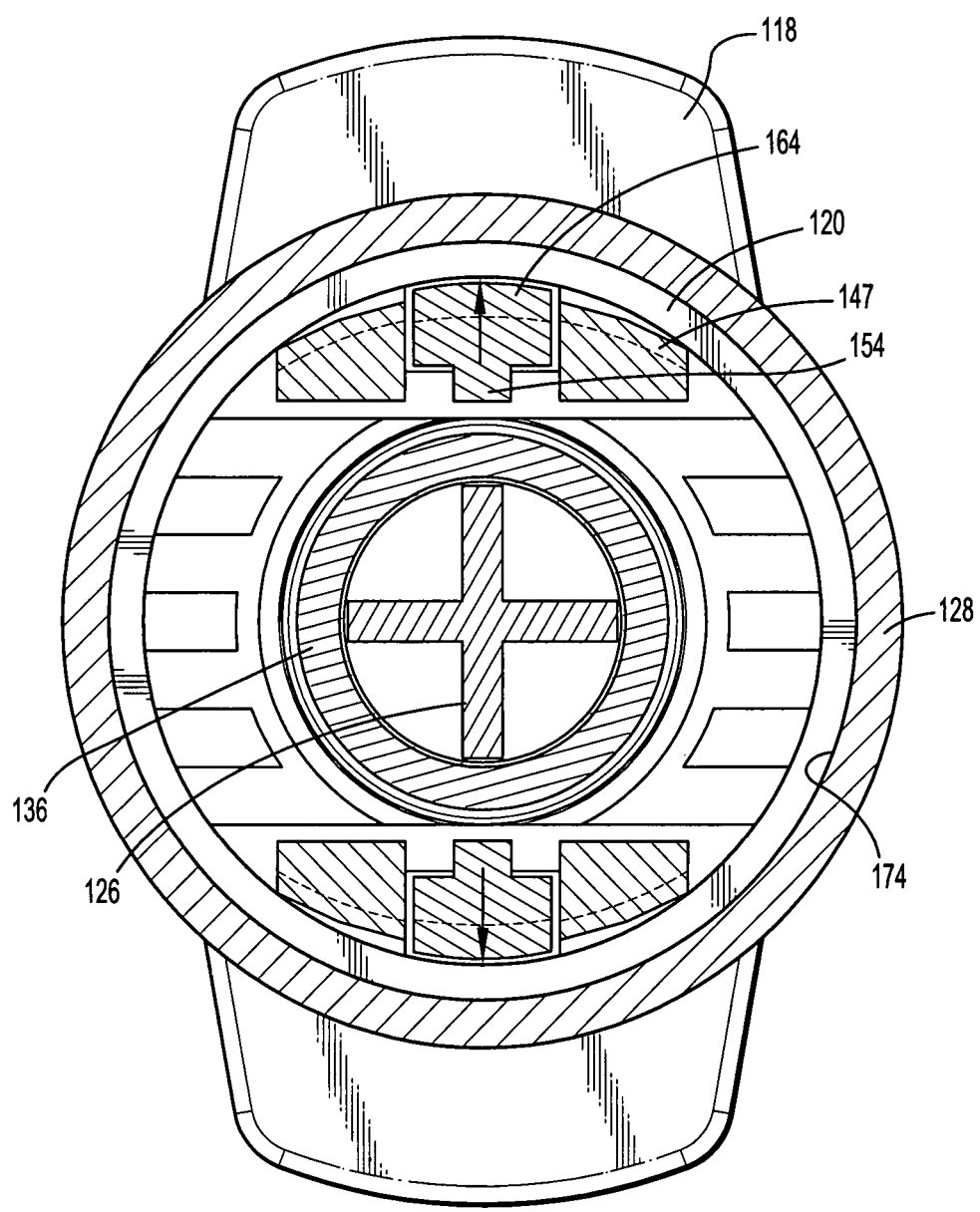
FIG. 33 is a cross-sectional view taken along section lines 30-30 of FIG. 24 after the plunger assembly has been moved to the advanced position.
Figure 33A:
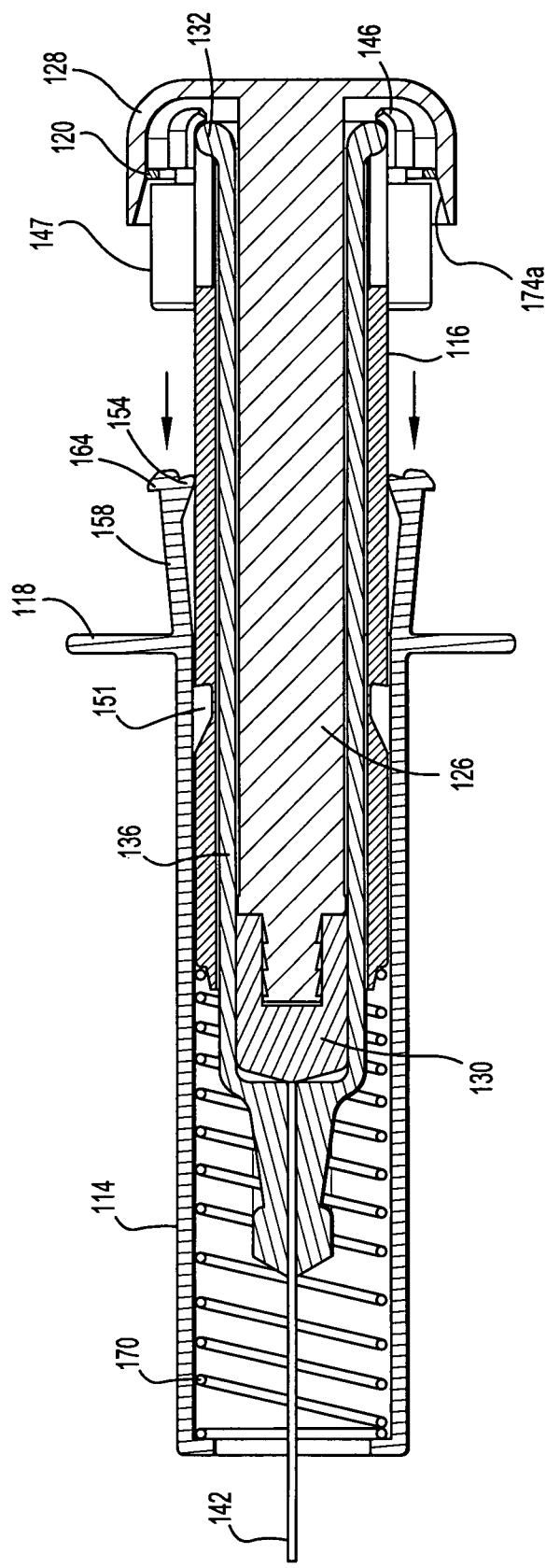
FIG. 33A is a cross-sectional view as shown in FIG. 32 as the outer sheath moves from the retracted position towards the advanced position.

Referring to FIGS. 31-33A, in use, when plunger assembly 122 nears its advanced position, interior surface 174 of plunger head 128 engages the portion of latch ring 120 defining major diameter d1 to deform latch ring 120 from its normal or undeformed substantially oval configuration to a substantially circular configuration. When this occurs, the portion of latch ring 120 defining minor diameter d2 moves radially outwardly to disengage latch ring 120 from projections 164 of fingers 158 (FIG. 33) to release outer sheath 114 from inner sheath 116. As illustrated, interior surface 174 may be tapered as at 174a to allow inner surface 174a to smoothly engage latch ring 120. When latch ring 120 disengages from projections 164 of fingers 158 of outer sheath 114, coil spring 170 urges outer sheath 114 towards its advanced position (FIG. 33A).

Figure 36:
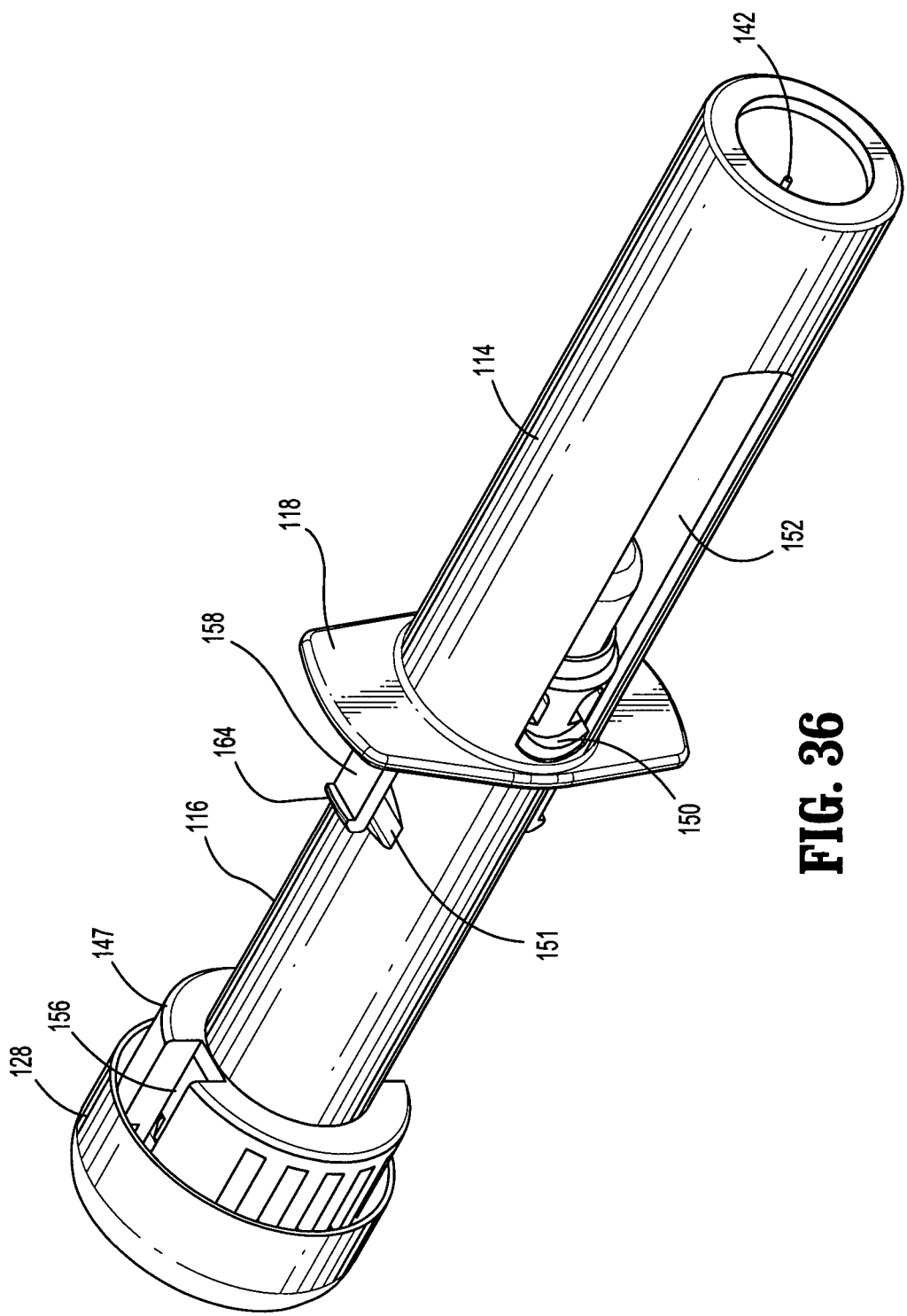
FIG. 36 is a side perspective view of the passive latch ring safety shield and injection device shown in FIG. 19 with the plunger assembly and the outer sheath in the advanced position.

Referring to FIG. 34-36, when outer sheath 114 reaches its advanced position, inwardly extending projections 154 formed on fingers 158 snap into cutouts 151 formed in body 144 of inner sheath 116. The positioning of projections 154 in cutouts 151, locks outer sheath 114 in its advanced position. As illustrated, mating surfaces of projections 154 and cutouts 151 are substantially perpendicular to a longitudinal axis of the shield assembly to prevent movement of outer sheath 114 back to its retracted position. As illustrated in FIG. 36, hollow needle 142 is positioned within and shielded by outer sheath 114 when outer sheath 114 is in its advanced position.

Figure 37:
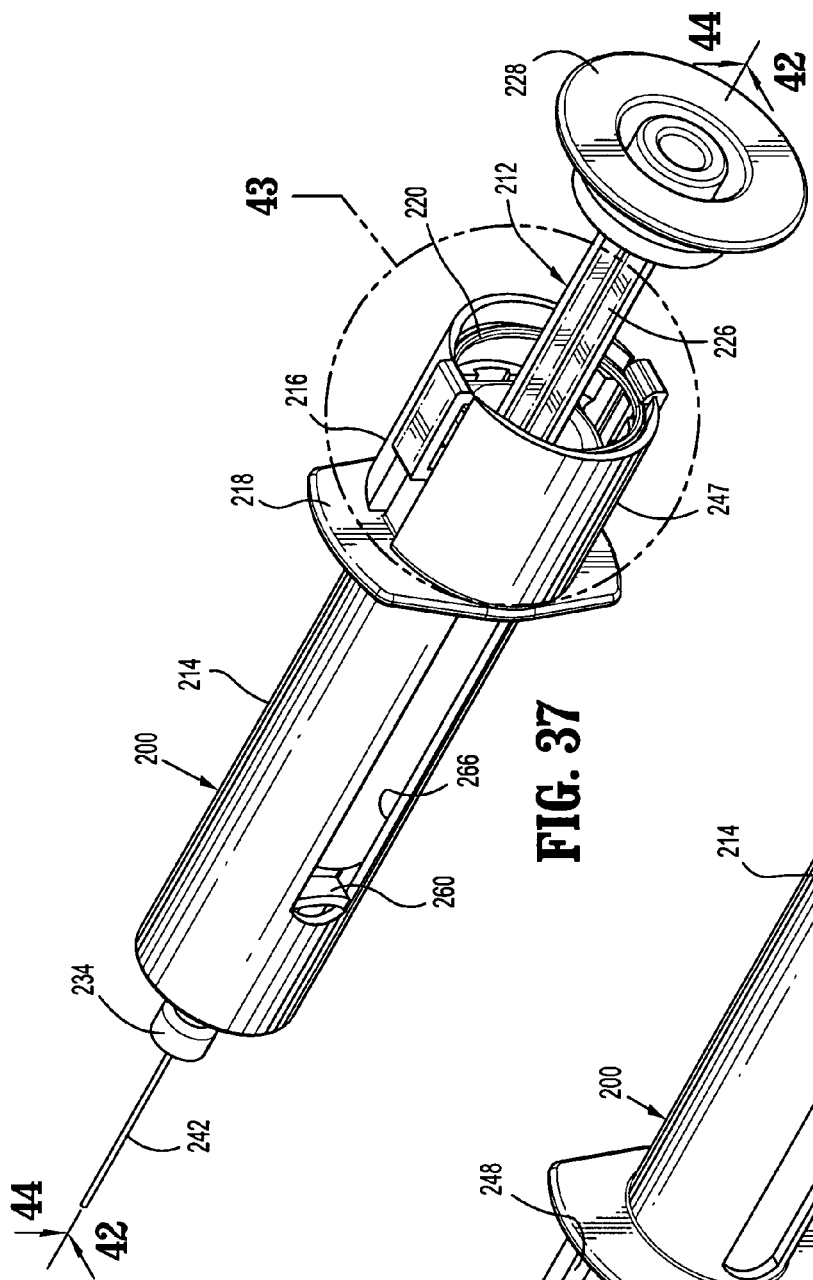
FIG. 37 is a perspective view from the proximal end of another embodiment of the presently disclosed passive latch ring safety shield assembly mounted on an injection device.
Figure 38:
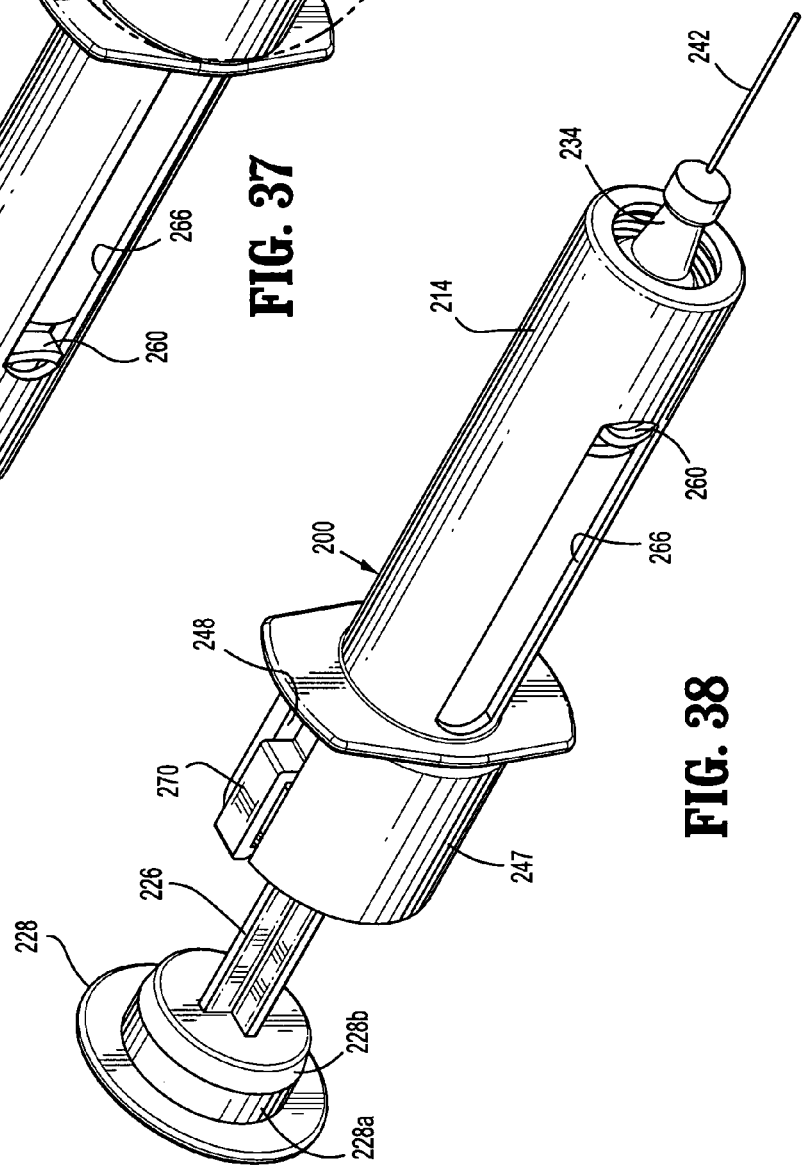
FIG. 38 is a perspective view from the distal end of the passive latch ring safety shield and injection device shown in FIG. 37.
Figure 39:
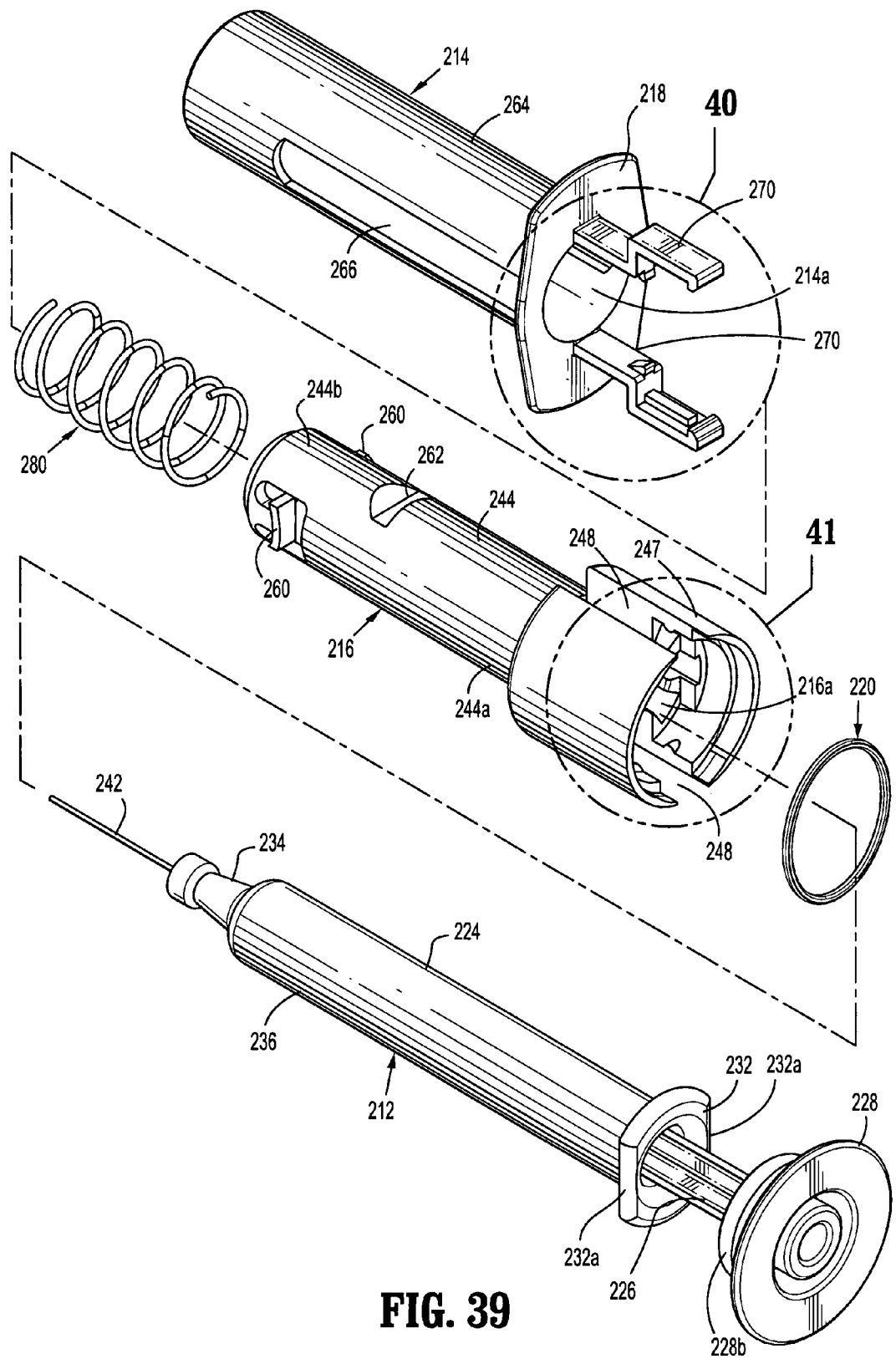
FIG. 39 is a perspective view with parts separated of the passive latch ring safety shield and injection device shown in FIG. 37.

FIGS. 37-53 illustrate another embodiment of the presently disclosed passive latch ring safety shield assembly ("shield assembly") shown generally as 200 mounted on an injection device 212, e.g. a prefilled syringe. Referring to FIGS. 37-39, shield assembly 200 includes an outer sheath 214, an inner sheath 216, and a latch ring 220. Outer sheath 214 includes a finger flange 218 and defines a longitudinal channel or throughbore 214a which is dimensioned to slidably receive inner sheath 216. Inner sheath 216 also defines a longitudinal channel or throughbore 216a which is dimensioned to receive injection device 212 as will be discussed in further detail below. Although outer sheath 214 and inner sheath 216 are shown as being substantially cylindrical, other configurations are envisioned, e.g., rectangular, oval, etc.

Figure 42:
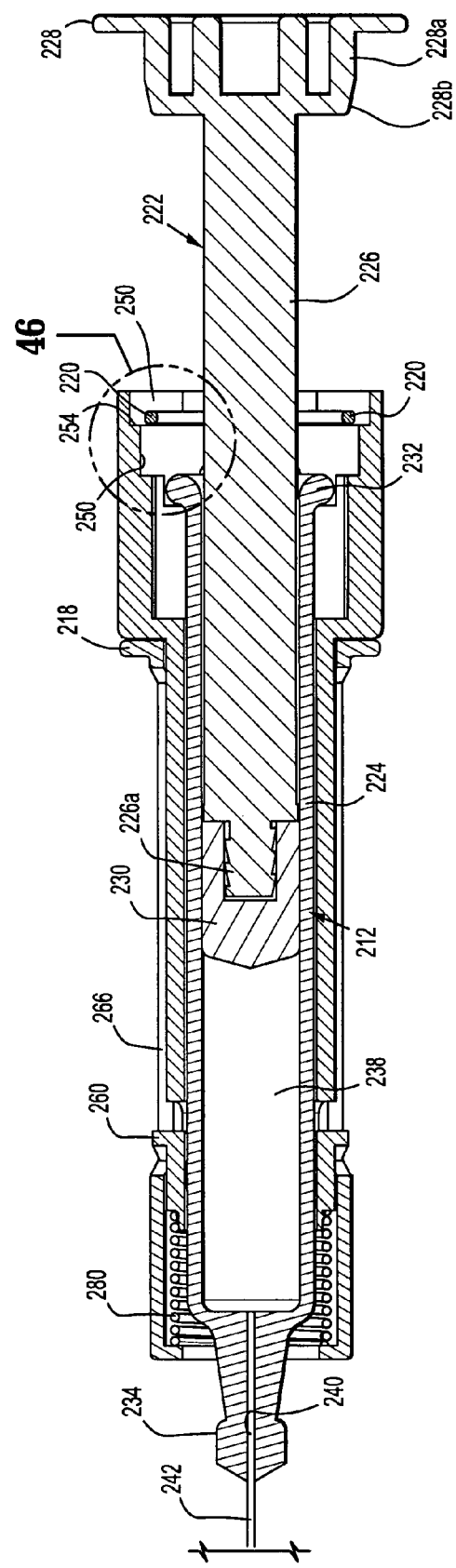
FIG. 42 is a cross-sectional view taken along section lines 42-42 of FIG. 37.

Referring also to FIG. 42, injection device 212 includes a plunger assembly 222 and a syringe body 224. Plunger assembly 222 includes a plunger rod 226, a head 228 formed on a proximal end of plunger rod 226 and a plunger 230 supported on a distal end of plunger rod 226. In one embodiment, plunger rod 226 and head 228 are integrally formed and plunger 230 is pressed onto a reduced diameter portion 226a of plunger rod 226. Alternately, other plunger assembly configurations are envisioned.

Syringe body 224 includes a proximal flange member 232, a distal hub portion 234, and a central barrel portion 236. Barrel portion 236 defines a fluid reservoir 238 (FIG. 42) and is dimensioned to be received within longitudinal channel 216a of inner sheath 216. Hub portion 234 defines a bore 240 (FIG. 42) which receives and supports a hollow needle 242. Bore 240 supports needle 242 such that needle 242 is fluidly connected with reservoir 238. In one embodiment, proximal flange member 232 defines a truncated disc which is engageable by a portion of inner sheath 216, as will be discussed in further detail below, to secure injection device 212 within channel 216a of inner sheath 216.

Figure 41:
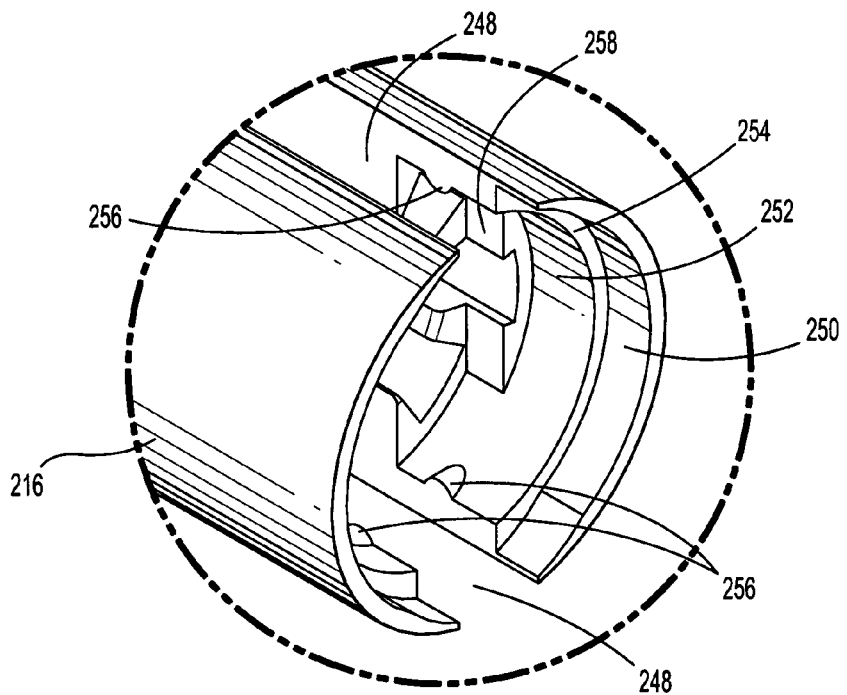
FIG. 41 is an enlarged view of the indicated area of detail shown in FIG. 39.

Referring to FIGS. 39 and 41, inner sheath 216 includes a tubular body 244 having a proximal end 244a and a distal end 244b. Proximal end 244a includes an enlarged head 247 which has diametrically opposed slots 248 which extend longitudinally through head 247. An inner periphery of head 247 defines a first annular surface 250 and a second annular surface 252 which are separated by a shoulder 254. Second annular surface 252 includes detents 256 adjacent each side of each slot 248 and diametrically opposed truncated surfaces or flats 258. Detents 256 facilitate retention of injection device 212 within head 247 of inner sheath 216. More specifically, proximal flange 232 is pressed into head 247 such that head 247 flexes slightly outwardly to allow flange 232 to pass over detents 256 and be retained within head 247 of inner sheath 216. When injection device 212 is secured within head 247 of inner sheath 216, flats 258 of head 247 engage flats sidewalls 232a (FIG. 39) of proximal flange 232 of syringe body 224 to prevent rotation of syringe body 224 within inner sheath 216.

Figure 43:
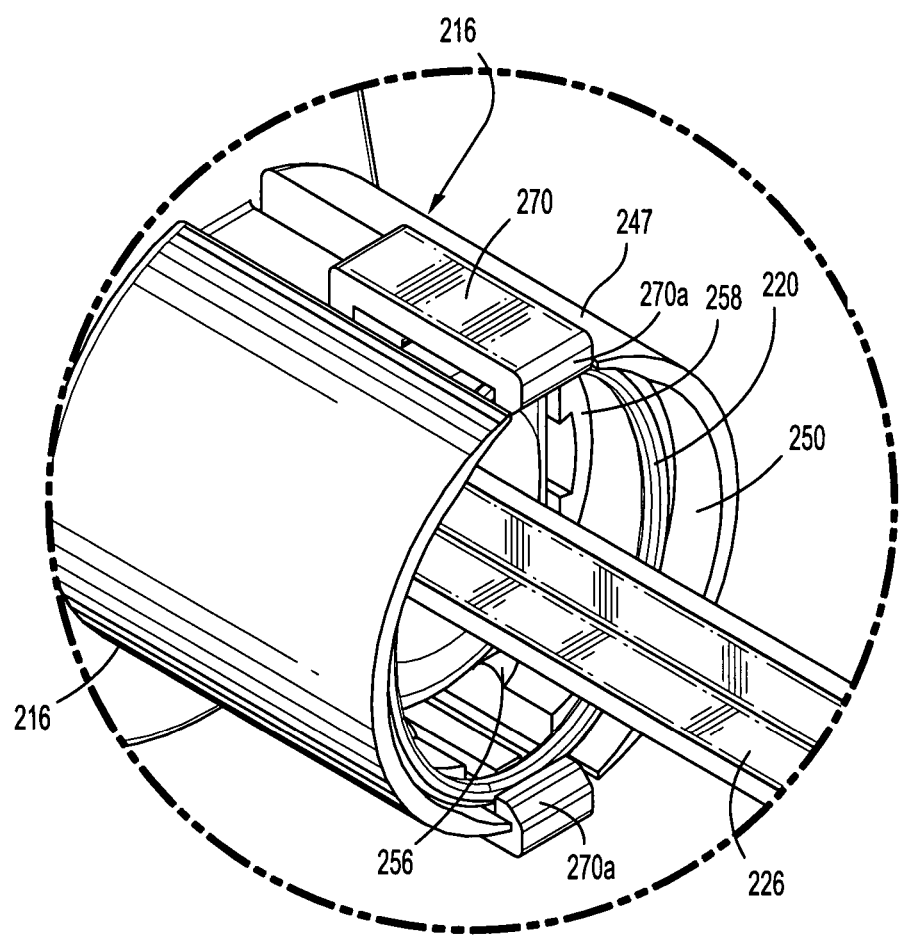
FIG. 43 is an enlarged view of the indicated area of detail shown in FIG. 37.
Figure 46:
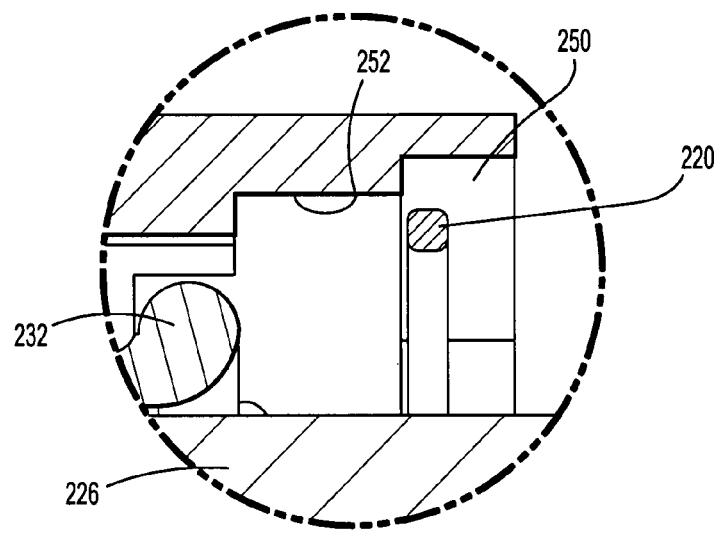
FIG. 46 is an enlarged view of the indicated area of detail shown in FIG. 42.
Figure 47:
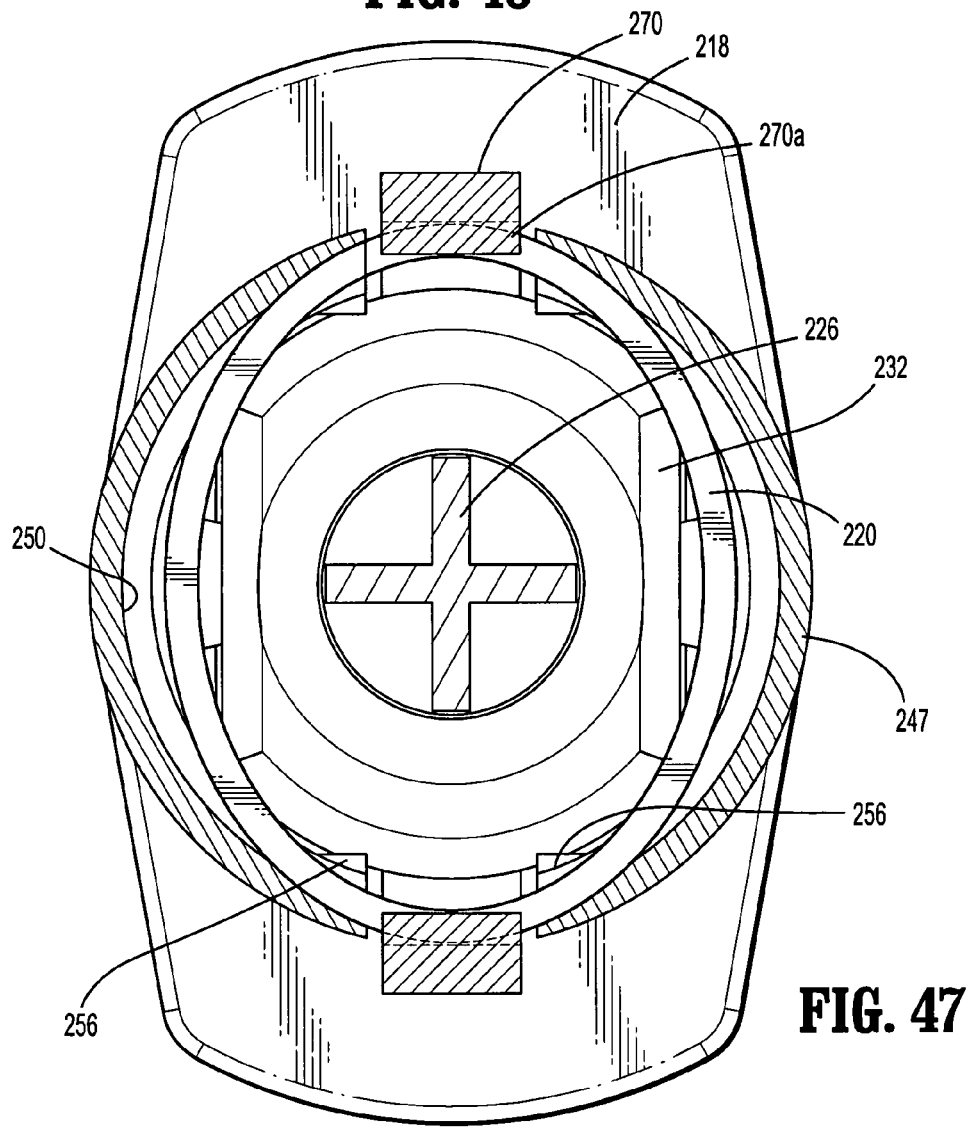
FIG. 47 is a cross-sectional view taken along section lines 47-47 of FIG. 45.
Figure 48:
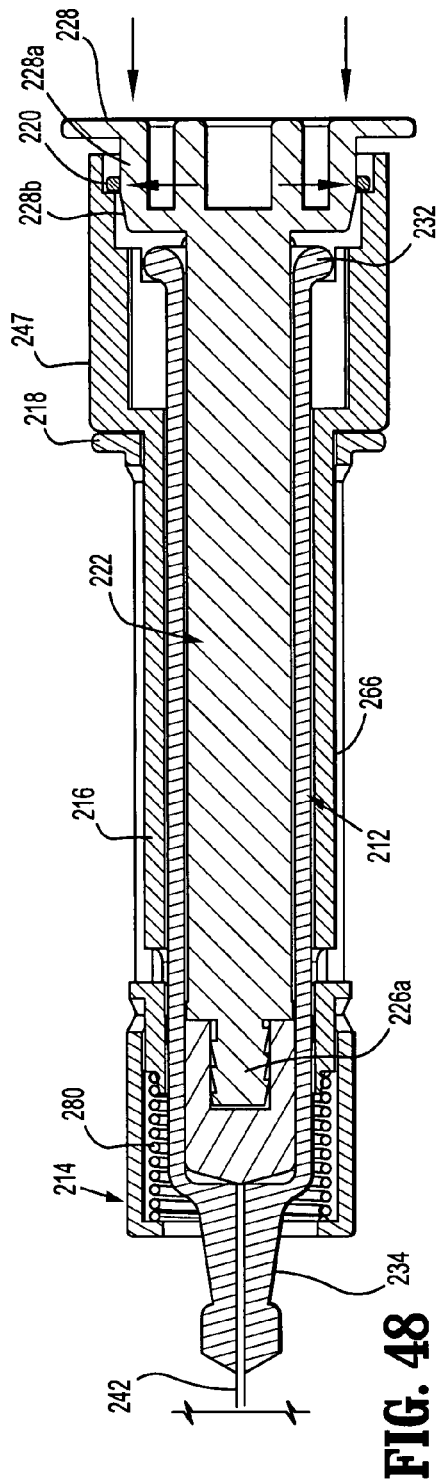
FIG. 48 is a cross-sectional view taken along section lines 42-42 of FIG. 37 with the plunger assembly moved to its advanced position.
Figure 49:
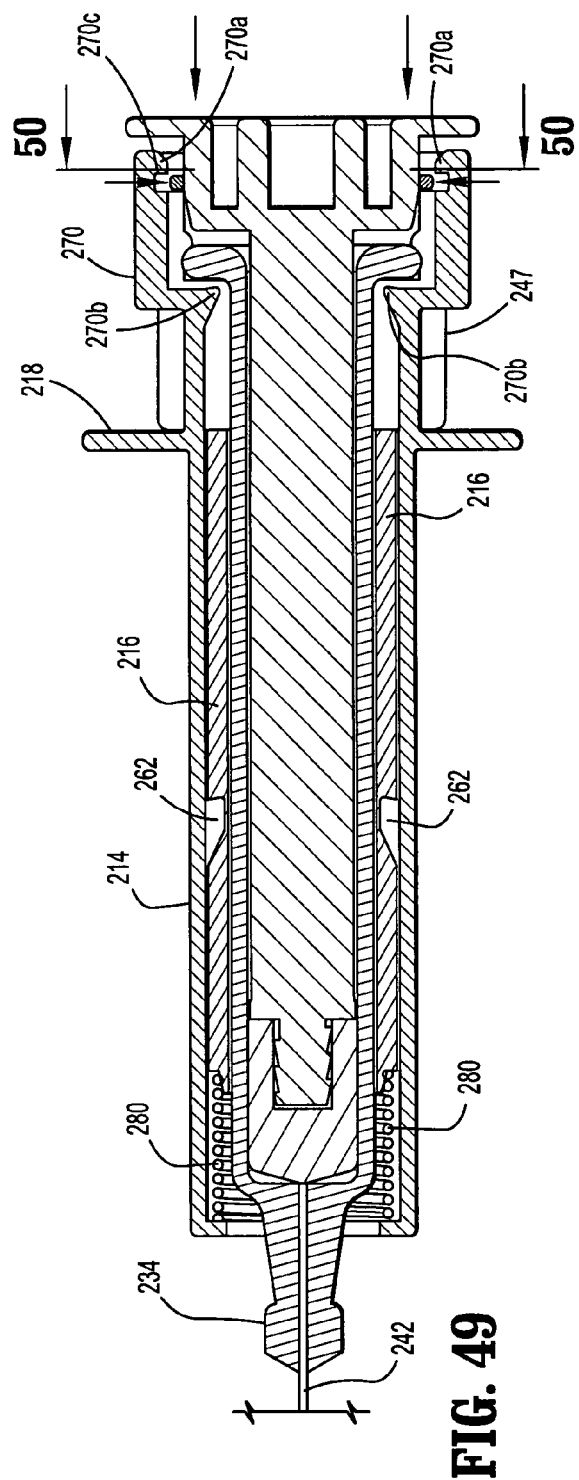
FIG. 49 is a cross-sectional view taken along section lines 44-44 of FIG. 37 with the plunger assembly moved to its advanced position.
Figure 50:
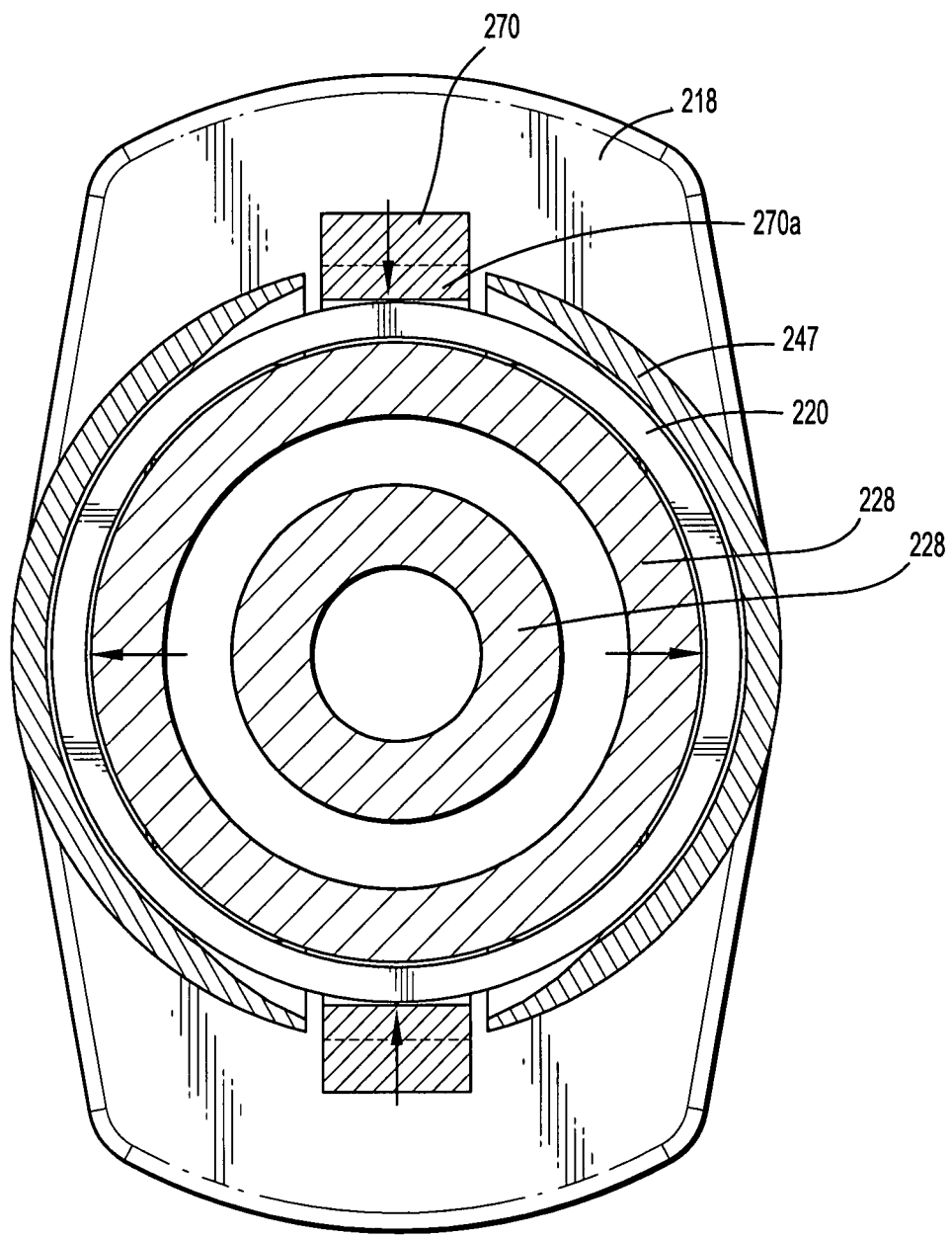
FIG. 50 is the cross-sectional view shown in FIG. 49 as the outer sheath moves towards its advanced position.
Figure 50A:
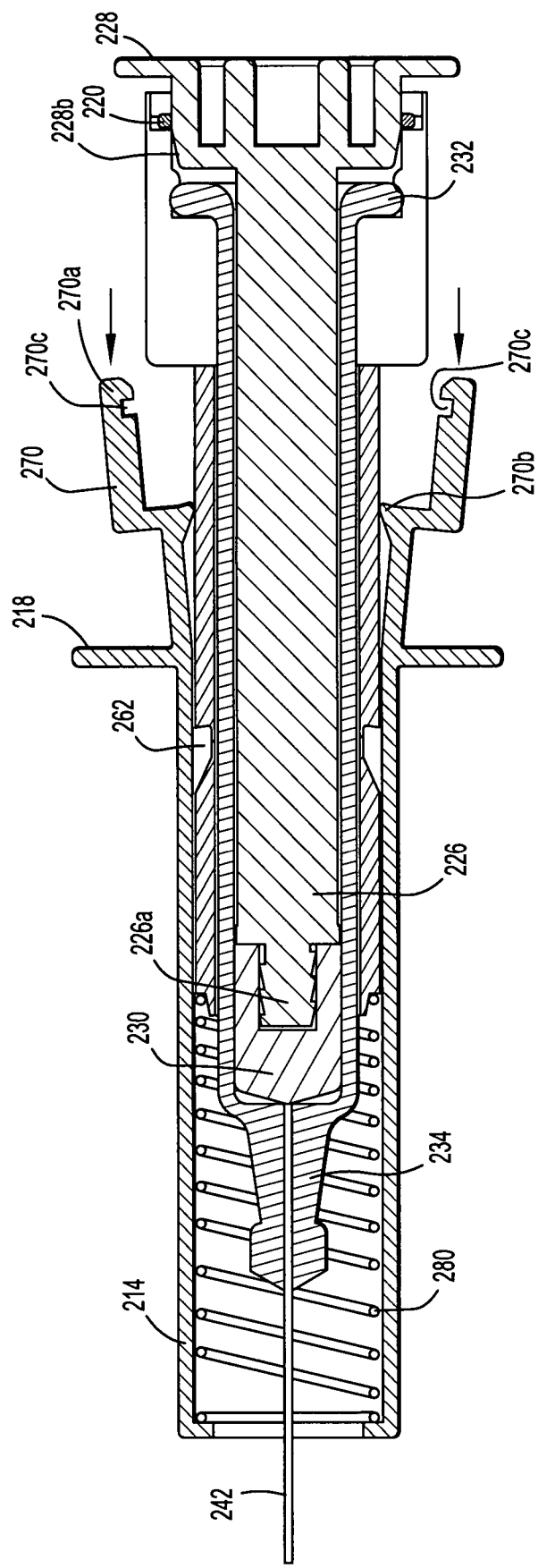

Referring also to FIG. 43, first annular surface 250 is dimensioned to receive latch ring 220 as will be discussed in further detail below. Latch ring 220 is supported on annular surface 250 and rests against shoulder 254 defined within head 247 of inner sheath 216.

Referring to FIG. 39, tubular body 244 of inner sheath 216 includes a pair of diametrically opposed projections 260 which extend radially outwardly from distal end 244b of inner sheath 216. Tubular body 244 also includes a pair of diametrically opposed cutouts 262 positioned between proximal and distal ends 244a and 244b of inner sheath 216. Projections 260 and cutouts 262 will be discussed in further detail below.

Figure 40:
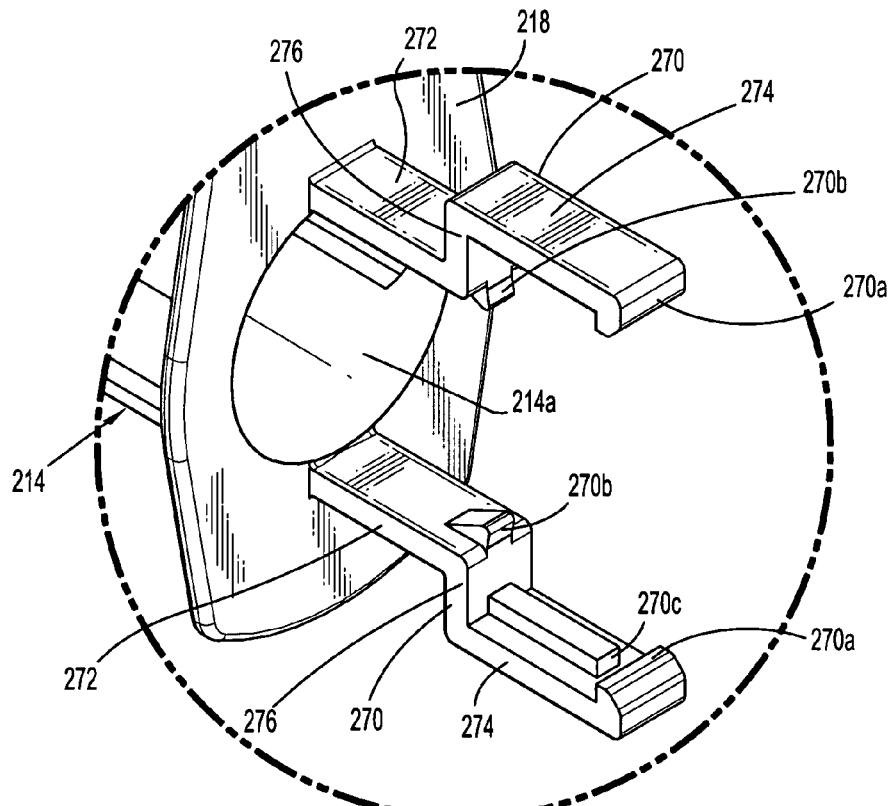
FIG. 40 is an enlarged view of the indicated area of detail shown in FIG. 39.

Referring to FIGS. 39 and 40, throughbore 214a of outer sheath 214 is dimensioned to slidably receive inner sheath 216. Outer sheath 214 includes a body 264 which defines a pair of diametrically opposed longitudinal slots 266. Each slot 266 is positioned and dimensioned to receive a respective projection 260 of inner sheath 216. Projections 260 and slots 266 facilitate movement of outer sheath 214 in relation to inner sheath 216 from a retracted position to an advanced position while preventing rotational movement of outer sheath 214 in relation to inner sheath 216. The ends of slots 266 act as stops to define the retracted and advanced positions of outer sheath 214.

Outer sheath 214 also includes a pair of fingers 270 (FIG. 40) which extend proximally from finger flange 218. Each finger 270 includes a proximally located engagement or hook portion 270a and a centrally located projection 270b. Each hook portion 270a defines a recess 270c dimensioned to receive latch ring 220. In one embodiment, finger 270 includes first and second longitudinally extending portions 272 and 274 which are interconnected by a transverse portion 276. Alternately, other finger configurations are envisioned, e.g., linear, curved, etc. Each finger 270 is positioned to be slidably received in a respective slot 248 of inner sheath 216, such that when outer sheath 214 is in its retracted position, hook portion 270a of finger 270 engages latch ring 220. Engagement between hook portion 270a and latch ring 220 retains outer sheath 214 in its retracted position against the urging of a biasing member 280, e.g., a coil spring 280 (FIG. 42). As discussed above with respect to biasing member 170 of shield assembly 100, biasing member 280 is positioned in compression between the distal end of outer sheath 214 and the distal end of inner sheath 216 to urge outer sheath 214 towards its advanced position (FIG. 42).

Referring briefly to FIG. 26, latch ring 220 is substantially identical to latch ring 120 of shield assembly 100 and includes a major diameter d1 and a minor diameter d2. When latch ring 220 is in its normal or undeformed configuration, latch ring 220 is substantially oval in shape. When latch ring 220 is supported on first annular surface 250 of inner sheath 216, the portions of latch ring 220 defining major diameter d1 extend across slots 248 to a position located within recesses 270c of hook portions 270a of fingers 270. See FIG. 43.

Referring to FIG. 42, head portion 228 of plunger assembly 222 includes a substantially cylindrical body portion 228a having a slightly tapered distal section 228b. As plunger assembly 222 of injection device 212 nears the end of its actuation stroke, body portion 228 of head portion 228 engages latch ring 220 to deform latch ring 220 from its substantially oval configuration to its substantially circular configuration. When this occurs, the portion of latch ring 220 defining major diameter portion d1 of latch ring 220 is drawn inwardly to disengage latch ring 220 from recesses 270c of hook portions 270a of fingers 270 and release outer sheath 214 from inner sheath 216.

Figure 53:
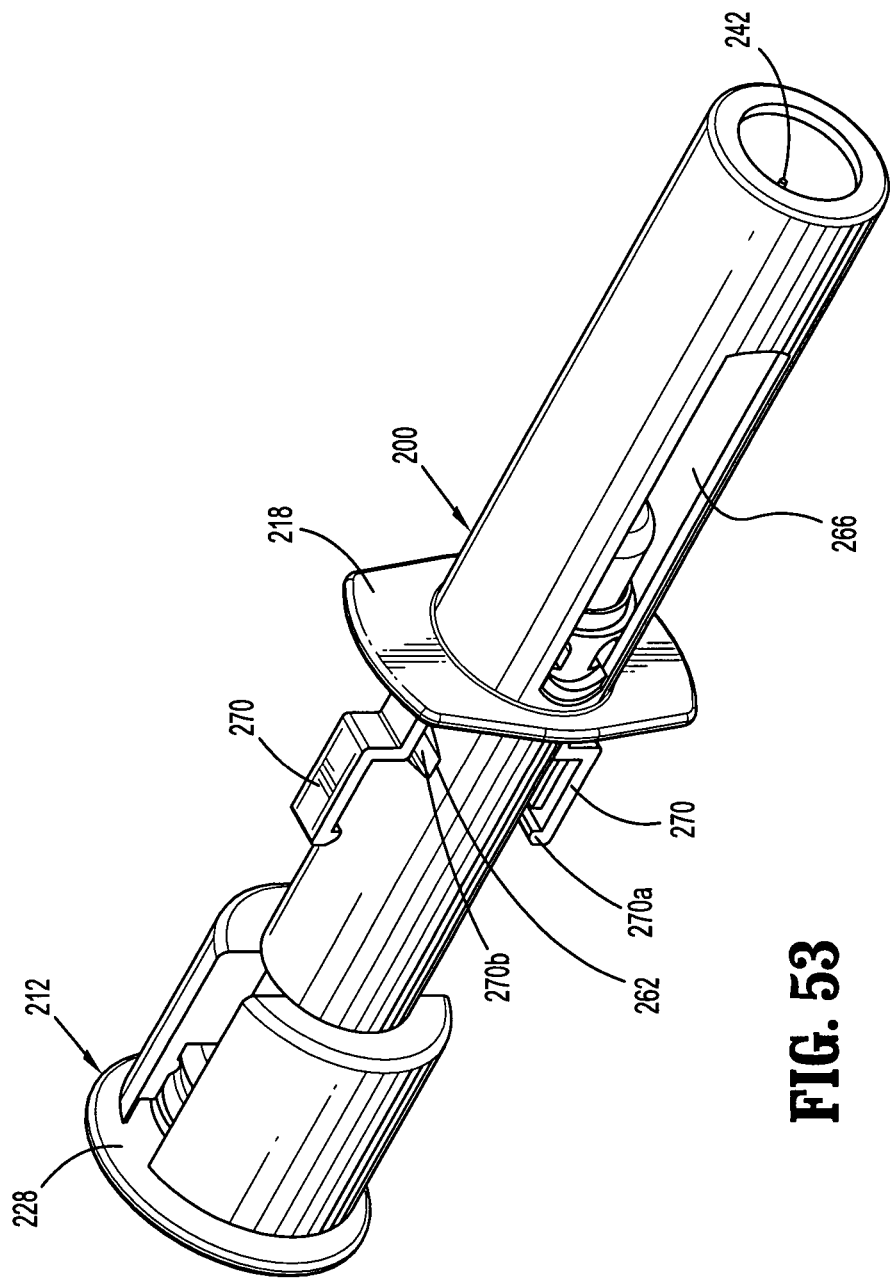
FIG. 53 is a perspective view from the distal end of the shield assembly shown in FIG. 37 with the outer sheath in its advanced position.

Referring to FIGS. 48-50A, in use, when injection device 212 is operated and plunger assembly 222 nears its advanced position, body portion 228a of head portion 228 of plunger assembly 222 engages the internal wall of latch ring 220 to deform latch ring 220 from its normal undeformed substantially oval configuration to a substantially circular configuration to draw the portion of latch ring 220 defining the major diameter d1 inwardly. When this occurs, latch ring 220 disengages from recess 270c of fingers 270 to allow biasing member 280 to urge outer sheath 214 distally in relation to inner sheath 216 as discussed above with respect to shield assemblies 10 and 100. As illustrated in FIGS. 51-53, in its advanced position, projections 270b of fingers 270 snap into cutouts 262 of inner sheath 216 to lock or retain outer sheath 214 in its advanced or extended position. In its extended position, outer sleeve 214 shields hollow needle 242 from inadvertent contact with medical personnel.

It will be understood that various modifications may be made to the embodiments disclosed herein. For example, although the above safety shield assemblies are is described in association with a prefilled syringe, it is envisioned that the safety shield may be suitable for use with other medical needle devices. Therefore, the above description should not be construed as limiting, but merely exemplifications of preferred embodiments. Those skilled in the art will envision other modifications within the scope and spirit of the claims appended hereto.

What is claimed is:

1. A passive safety shield device comprising:
   an inner sheath having a proximal end and a distal end and defining a longitudinal channel which extends between the proximal and distal ends and is dimensioned to receive an injection device having a plunger;
   an outer sheath having a proximal end and a distal end and defining a longitudinal channel dimensioned to slidably receive the inner sheath;
   a biasing member supported within the outer sheath, the biasing member being positioned to urge the outer sheath from a retracted position to an advanced position in relation to the inner sheath; and
   a deformable ring positioned on the proximal end of the safety shield device, the deformable ring being deformable from an undeformed condition to a deformed condition in response to actuation of the plunger of the injection device, the deformable ring in its undeformed condition being configured to retain the outer sheath in the retracted position;
   wherein in its deformed condition, the deformable ring is configured to allow movement of the outer sheath in relation to the inner sheath from the retracted position to the advanced position.

2. A passive safety shield device according to claim 1, wherein the deformable ring is supported on the outer sheath and is positioned to abut a shoulder on the inner sheath in its undeformed condition to retain the outer sheath in the retracted position.

3. A passive safety shield device according to claim 2, wherein the deformable ring is supported within an annular recess formed about the proximal end of the outer sheath.

4. A passive safety shield device according to claim 3, wherein the annular recess includes at least one opening and the deformable ring includes at least one projection, the at least one projection being positioned in the at least one opening.

5. A passive safety shield device according to claim 4, wherein the at least one opening includes a plurality of openings and the at least one projection includes a plurality of projections.

6. A passive safety shield device according to claim 3, wherein the deformable ring is substantially oval in its undeformed condition and substantially circular in its deformed condition.

7. A passive safety shield device according to claim 2, wherein the deformable ring is substantially oval in its undeformed condition and substantially circular in its deformed condition.

8. A passive safety shield device according to claim 2, wherein the inner sheath includes a cutout positioned to receive the deformable ring when the outer sheath is in the advanced position to retain the outer sheath in the advanced position.

9. A passive safety shield device according to claim 1, wherein the deformable ring is substantially oval in its undeformed condition and substantially circular in its deformed condition.

10. A passive safety shield device according to claim 1, further including a collar supported on the outer sheath, the collar having at least one finger flange.

11. A passive safety shield device according to claim 1, wherein the inner sheath includes at least one engagement member configured to engage an injection device to secure the inner sheath to the injection device.

12. A passive safety shield device according to claim 11, wherein the at least one engagement member includes a flexible arm having an engaging portion configured to engage a portion of the injection device.

13. A passive safety shield device according to claim 12, wherein the at least one engagement member includes first and second diametrically opposed engagement members.

14. A passive safety shield device according to claim 1, wherein the outer sheath includes at least one guide channel dimensioned to slidably receive at least one longitudinal rib formed on the inner sheath.

15. A passive safety shield device according to claim 14, wherein the at least one guide channel includes a pair of guide channels and the at least one longitudinal rib includes a pair of longitudinal ribs.

16. A passive safety shield device according to claim 1, wherein the deformable ring is supported on the inner sheath and is positioned to abut at least one inwardly extending projection formed on the outer sheath.

17. A passive safety shield device according to claim 16, wherein the outer sheath include a pair of proximally extending fingers, each of the fingers having one of the at least one projection positioned thereon.

18. A passive safety shield device according to claim 17, wherein the pair of proximally extending fingers are received within a pair of slots formed in the proximal end of the inner sheath.

19. A passive safety shield device according to claim 18, wherein the deformable ring is supported on the inner sheath such that the deformable ring extends across each slot of the pair of slots.

20. An injection device according to claim 19, wherein the at least one engagement member includes a pair of diametrically opposed flexible arms, each of the arms including a hook portion positioned to snap over and engage the proximal flange of the barrel portion of the injection device.

21. A passive safety shield device according to claim 16, wherein the deformable ring is substantially oval in its undeformed condition and substantially circular in its deformed condition.

22. A passive safety shield device according to claim 16, wherein the inner sheath includes a plurality of proximally extending arms configured to engage an injection device.

23. A passive safety shield device according to claim 22, wherein each of the plurality of arms includes a hook portion configured to engage an injection device.

24. A passive safety shield device according to claim 23, wherein each of the plurality of arms includes a recess which is dimensioned to receive the deformable ring.

25. A passive safety shield device according to claim 16, wherein the inner sheath includes a plurality of recesses dimensioned to receive the deformable ring.

26. A passive safety shield device according to claim 16, wherein the inner sheath includes a head portion having an inner periphery including at least one detent for retaining an injection device within the head portion.

27. A passive safety shield device according to claim 16, wherein the inner sheath includes a head portion having first and second annular surfaces which are separated by a shoulder, the deformable ring being supported within the first annular surface adjacent the shoulder.

28. A passive safety shield device according to claim 16, wherein the head portion includes a pair of diametrically located slots, the deformable ring being positioned to extend across the slots.

29. A passive safety shield device according to claim 28, wherein the outer sheath includes two proximally extending fingers positioned to move within the pair of slots, each of the fingers including an engagement portion for engaging the deformable ring.

30. A passive safety shield according to claim 29, wherein the inner sheath includes as least one cutout and the outer sheath includes at least one projection, the at least one projection being positioned and dimensioned to be received within the at least one cutout to retain the outer sheath in the advanced position in relation to the inner sheath.

31. An injection device and passive safety shield assembly comprising:
    an injection device including a barrel portion defining a fluid reservoir, a hub portion supporting a hollow needle, and a plunger assembly including a plunger head;
    an inner sheath having a proximal end and a distal end and defining a longitudinal channel which extends between the proximal and distal ends and is dimensioned to receive the injection device;
    an outer sheath having a proximal end and a distal end and defining a longitudinal channel dimensioned to slidably receive the inner sheath;
    a biasing member supported within the outer sheath, the biasing member being positioned to urge the outer sheath from a retracted position to an advanced position in relation to the inner sheath; and
    a deformable ring positioned on the safety shield device, the deformable ring being positioned to engage the plunger assembly of the injection device and being deformable from an undeformed condition to a deformed condition in response to actuation of the plunger assembly of the injection device, the deformable ring in its undeformed condition being configured to retain the outer sheath in the retracted position;

wherein in its deformed condition, the deformable ring is configured to allow movement of the outer sheath in relation to the inner sheath from the retracted position to the advanced position.

32. An injection device and passive safety shield assembly according to claim 31, wherein the deformable ring is supported on the outer sheath and is positioned to abut a shoulder on the inner sheath in its undeformed condition to retain the outer sheath in the retracted position.

33. An injection device and passive safety shield assembly as recited in claim 32, wherein the plunger assembly is movable in relation to the barrel portion from a retracted position to an advanced position, the plunger head including an extended portion positioned to engage the deformable ring when the plunger assembly nears its advanced position.

34. An injection device and passive safety shield assembly according to claim 31, wherein the barrel portion of the injection device includes a proximal flange and the inner sheath includes at least one engagement member positioned to engage the proximal flange to mount the inner sheath about the injection device.

* * * * *